United States Patent
Leinfelder et al.

(10) Patent No.: US 6,218,168 B1
(45) Date of Patent: Apr. 17, 2001

(54) PROCESS FOR PREPARING O-ACETYLSERINE, L-CYSTEINE AND L-CYSTEINE-RELATED PRODUCTS

(75) Inventors: Walfred Leinfelder, München; Peter Heinrich, Todtenweis-Sand, both of (DE)

(73) Assignee: Consortium für elektrochemische Inudstrie GmbH, Munich (DE)

( * ) Notice: Subject to any disclaimer, the term of this patent is extended or adjusted under 35 U.S.C. 154(b) by 0 days.

(21) Appl. No.: 09/065,104

(22) PCT Filed: Oct. 24, 1996

(86) PCT No.: PCT/EP96/04613

§ 371 Date: May 13, 1998

§ 102(e) Date: May 13, 1998

(87) PCT Pub. No.: WO97/15673

PCT Pub. Date: May 1, 1997

(30) Foreign Application Priority Data

Oct. 26, 1995 (DE) .............................. 195 39 952

(51) Int. Cl.[7] .............................. C12N 1/20; C12N 9/10; C12N 15/00; C07H 21/04; C07K 1/00

(52) U.S. Cl. .................. 435/252.3; 435/193; 435/320.1; 536/23.2; 536/23.7; 530/350

(58) Field of Search .................. 435/193, 252.3, 435/320.1; 536/23.2, 23.7; 530/350

(56) References Cited

U.S. PATENT DOCUMENTS 4,965,197   10/1990   Liebel et al. ..................... 435/69.8

OTHER PUBLICATIONS

Denk et al. J. Gen. Microbiol. (1987) : 133 : 515–525.*

* cited by examiner

*Primary Examiner*—Tekchand Saidha
(74) *Attorney, Agent, or Firm*—Collard & Roe, P.C.

(57) ABSTRACT

A process is for preparing O-acetylserine, L-cysteine and sulphurous compounds derived therefrom using feedback-resistant serine acetyl transferases. In comparison with the wild-type enzyme, these serine acetyl transferases have reduced sensitivity to the inhibitor L-cysteine and a protein sequence which, in comparison with the wild-type enzyme, displays at least one mutation or deletion. The process has a mutation which lies in the sequence region of the amino acid in position 97 up to and including the amino acid in position 273 or the deletion lies in the carboxy terminal sequence region as from the amino acid in position 227, position 1 being the starter methionine of FIG. 5 (SEQ ID NO:1) and the mutation from Met to Ile in position 256 being excluded.

6 Claims, 12 Drawing Sheets

Fig. 5

```
  1  MSCEELEIVW NNIKAEARTL ADCEPMLASF YHATLLKHEN LGSALSYMLA
 51  NKLSSPIMPA IAIREVVEEA YAADPEMIAS AACDIQAVRT RDPAVDKYST
101  PLLYLKGFHA LQAYRIGHWL WNQGRRALAI FLQNQVSVTF QVDIHPAAKI
151  GRGIMLDHAT GIVVGETAVI ENDVSILQSV TLGGTGKSGG DRHPKIREGV
201  MIGAGAKILG NIEVGRGAKI GAGSVVLQPV PPHTTAAGVP ARIVGKPDSD
251  KPSMDMDQHF NGINHTFEYG DGI
```

Fig. 6

```
   1  TCCGCGAACTGGCGCATCGCTTCGGCGTTGAAATGCCAATAACCGAGGAAATTTATCAAG

61  TATTATATTGCGGAAAAAACGCGCGCGAGGCAGCATTGACTTTACTAGGTCGTGCACGCA

121  AGGACGAGCGCAGCAGCCACTAACCCCAGGGAACCTTTGTTACCGCTATGACCCGGCCCG

181  CGCAGAACGGGCCGGTCATTATCTCATCGTGTGGAGTAAGCAATGTCGTGTGAAGAACTG
   1                                                MetSerCysGluGluLeu

241  GAAATTGTCTGGAACAATATTAAAGCCGAAGCCAGAACGCTGGCGGACTGTGAGCCAATG
   7  GluIleValTrpAsnAsnIleLysAlaGluAlaArgThrLeuAlaAspCysGluProMet

301  CTGGCCAGTTTTTACCACGCGACGCTACTCAAGCACGAAAACCTTGGCAGTGCACTGAGC
  27  LeuAlaSerPheTyrHisAlaThrLeuLeuLysHisGluAsnLeuGlySerAlaLeuSer

361  TACATGCTGGCGAACAAGCTGTCATCGCCAATTATGCCTGCTATTGCTATCCGTGAAGTG
  47  TyrMetLeuAlaAsnLysLeuSerSerProIleMetProAlaIleAlaIleArgGluVal

421  GTGGAAGAAGCCTACGCCGCTGACCCGGAAATGATCGCCTCTGCGGCCTGTGATATTCAG
  67  ValGluGluAlaTyrAlaAlaAspProGluMetIleAlaSerAlaAlaCysAspIleGln

481  GCGGTGCGTACCCGCGACCCGGCAGTCGATAAATACTCAACCCCGTTGTTATACCTGAAG
  87  AlaValArgThrArgAspProAlaValAspLysTyrSerThrProLeuLeuTyrLeuLys

541  GGTTTTCATGCCTTGCAGGCCTATCGCATCGGTCACTGGTTGTGGAATCAGGGGCGTCGC
 107  GlyPheHisAlaLeuGlnAlaTyrArgIleGlyHisTrpLeuTrpAsnGlnGlyArgArg

601  GCACTGGCAATCTTTCTGCAAAACCAGGTTTCTGTGACGTTCCAGGTCGATATTCACCCG
 127  AlaLeuAlaIlePheLeuGlnAsnGlnValSerValThrPheGlnValAspIleHisPro

661  GCAGCAAAAATTGGTCGCGGTATCATGCTTGACCACGCGACAGGCATCGTCGTTGGTGAA
 147  AlaAlaLysIleGlyArgGlyIleMetLeuAspHisAlaThrGlyIleValValGlyGlu

721  ACGGCGGTGATTGAAAACGACGTATCGATTCTGCAATCTGTGACGCTTGGCGGTACGGGT
 167  ThrAlaValIleGluAsnAspValSerIleLeuGlnSerValThrLeuGlyGlyThrGly

781  AAATCTGGTGGTGACCGTCACCCGAAAATTCGTGAAGGTGTGATGATTGGCGCGGGCGCG
 187  LysSerGlyGlyAspArgHisProLysIleArgGluGlyValMetIleGlyAlaGlyAla

841  AAAATCCTCGGCAATATTGAAGTTGGGCGCGGCGCGAAGATTGGCGCAGGTTCCGTGGTG
 207  LysIleLeuGlyAsnIleGluValGlyArgGlyAlaLysIleGlyAlaGlySerValVal

901  CTGCAACCGGTGCCGCCGCATACCACCGCCGCTGGCGTTCCGGCTCGTATTGTCGGTAAA
 227  LeuGlnProValProProHisThrThrAlaAlaGlyValProAlaArgIleValGlyLys

961  CCAGACAGCGATAAGCCATCAATGGATATGGACCAGCATTTCAACGGTATTAACCATACA
 247  ProAspSerAspLysProSerMetAspMetAspGlnHisPheAsnGlyIleAsnHisThr

1021  TTTGAGTATGGGGATGGGATCTAATGTCCTGTGATCGTGCCGGATGCGATGTAATCATCT
 267  PheGluTyrGlyAspGlyIleEnd

1081  ATCCGGCCTACAGTAACTAATCTCTCAATACCGCTCCCGGATACCCCAACTGTCG-1135
```

Restriction map of the plasmid pP1 pUC18;  chromosomal DNA; PL: Polylinker

5'-GCCTGGATCCTGCAGTCGACCTGGCGCATCGCTTCGGCGTTG-3'

Fig. 10

5'-GTAGGAGCTCTGCAGAATTCGGGTATCCGGGAGCGGTATTG-3'

Fig. 11

5'-TGGACCAGAGCTCTGGCTGGCGCATCGCTTCGGCGTTG-3'

Fig. 13

5'-CTCGATGCATTACGTAGGGGTATCCGGGAGCGGTATTG-3'

Fig. 15

Tab. 3: Oligonucleotides which were used for the site-specific mutation for generating new feedback-resistant cysE alleles

| SEQ ID NO: | Mutation oligo-nucleotides | Nucleotide sequence | Position in Fig. 6 | Amino acid substitution |
|---|---|---|---|---|
| 5 | cysE-Mut-1 | 5'-GCCGCTAGCGTTCCGGCT-3' | 928-945 | GLY238->Ser238 |
| 6 | cysE-Mut-3 | 5'-CCGCCGCATACCACCGCCGTT-3' | 913-933 | Ala237->Val237 |
| 7 | cysE-Mut-6 | 5'-CCATCAATGGATATAGACCAGCAT-3' | 976-999 | Met256->Ile256 |
| 8 | cysE-Mut-10 | 5'-GTCGTTGGTGAAGCGGCGGTGATT-3' | 709-732 | Thr167->Ala167 |

Fig. 12

Tab. 5: Antisense oligonucleotides for preparing cysE alleles possessing carboxyterminal deletions

| SEQ ID. | Mutation oligonucleotide | Nucleotide sequence | Position in Fig. 6 |
|---|---|---|---|
| 10 | cysE-Del270 | 5'-CTCGATGCATTACGTATTACCCATACTCAAATCTATGGTTAATACC-3' | 1006-1032 |
| 11 | cysE-Del268 | 5'-CTCGATGCATTACGTATTACTCAAATGTATGGTTAATACCGTTGAA-3' | 1000-1026 |
| 12 | cysE-Del263 | 5'-CTCGATGCATTACGTATTAAATACCGTTGAAATGCTGGTCCATATC-3' | 985-1011 |
| 13 | cysE-Del259 | 5'-CTCGATGCATTACGTATTAATGCTGGTCCATATCCATTGATGGCTT-3' | 973- 999 |
| 14 | cysE-Del258 | 5'-CTCGATGCATTACGTATTACTGGTCCATATCCATTGATGGCTTATC-3' | 970- 996 |
| 15 | cysE-Del257 | 5'-CTCGATGCATTACGTATTAGTCCATATCCATTGATGGCTTATCGCTG-3' | 966- 993 |
| 16 | cysE-Del256 | 5'-CTCGATGCATTACGTATTACATATCCATTGATGGCTTATCGCTGTC-3' | 964- 990 |
| 17 | cysE-Del255 | 5'-CTCGATGCATTACGTATTAATCCATTGATGGCTTATCGCTGTCTGG-3' | 961- 987 |
| 18 | cysE-Del250 | 5'-CTCGATGCATTACGTATTAATCGCTGTCTGGTTTACCGACAATACG-3' | 946- 972 |
| 19 | cysE-Del249 | 5'-CTCGATGCATTACGTATTAGCTGTCTGGTTTACCGACAATACGAGC-3' | 943- 969 |
| 20 | cysE-Del248 | 5'-CTCGATGCATTACGTATTAGTCTGGTTTACCGACAATACGAGCCGG-3' | 940- 966 |
| 21 | cysE-Del245 | 5'-CTCGATGCATTACGTATTAACCGACAATACGAGCCGGAACGCCAGC-3' | 931- 957 |
| 22 | cysE-Del239 | 5'-CTCGATGCATTACGTATTAAACGCCAGCGGGTGGTATCCGGCGG-3' | 913- 939 |
| 23 | cysE-Del227 | 5'-CTCGATGCATTACGTATTACAGCACCACGGAACCTGCGCCAATCTT-3' | 877- 903 |

FIG. 14

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 273 amino acids
      (B) TYPE: amino acids
      (C) STRANDEDNESS:
      (D) TOPOLOGY: linear (ii) MOLECULE TYPE: protein (vi) ORIGINAL SOURCE:
      (A) ORGANISM: Escherichia coli
      (B) STRAIN: W3110

(xi) SEQUENCE DESCRIPTION: SEQ ID NO: 1:

```
Met Ser Cys Glu Glu Leu Glu Ile Val Trp Asn Asn Ile Lys Ala Glu
1               5                   10                  15

Ala Arg Thr Leu Ala Asp Cys Glu Pro Met Leu Ala Ser Phe Tyr His
            20                  25                  30

Ala Thr Leu Leu Lys His Glu Asn Leu Gly Ser Ala Leu Ser Tyr Met
        35                  40                  45

Leu Ala Asn Lys Leu Ser Ser Pro Ile Met Pro Ala Ile Ala Ile Arg
    50                  55                  60

Glu Val Val Glu Glu Ala Tyr Ala Ala Asp Pro Glu Met Ile Ala Ser
65                  70                  75                  80

Ala Ala Cys Asp Ile Gln Ala Val Arg Thr Arg Asp Pro Ala Val Asp
                85                  90                  95

Lys Tyr Ser Thr Pro Leu Leu Tyr Leu Lys Gly Phe His Ala Leu Gln
            100                 105                 110

Ala Tyr Arg Ile Gly His Trp Leu Trp Asn Gln Gly Arg Arg Ala Leu
        115                 120                 125

Ala Ile Phe Leu Gln Asn Gln Val Ser Val Thr Phe Gln Val Asp Ile
    130                 135                 140

His Pro Ala Ala Lys Ile Gly Arg Gly Ile Met Leu Asp His Ala Thr
145                 150                 155                 160

Gly Ile Val Val Gly Glu Thr Ala Val Ile Glu Asn Asp Val Ser Ile
                165                 170                 175

Leu Gln Ser Val Thr Leu Gly Gly Thr Gly Lys Ser Gly Gly Asp Arg
            180                 185                 190

His Pro Lys Ile Arg Glu Gly Val Met Ile Gly Ala Gly Ala Lys Ile
        195                 200                 205

Leu Gly Asn Ile Glu Val Gly Arg Gly Ala Lys Ile Gly Ala Gly Ser
    210                 215                 220

Val Val Leu Gln Pro Val Pro Pro His Thr Thr Ala Ala Gly Val Pro
225                 230                 235                 240
```

```
Ala Arg Ile Val Gly Lys Pro Asp Ser Asp Lys Pro Ser Met Asp Met
                245                 250                 255

Asp Gln His Phe Asn Gly Ile Asn His Thr Phe Glu Tyr Gly Asp Gly
            260                 265                 270

Ile
```

(2) INFORMATION FOR SEQ ID NO: 2:

(i) SEQUENCE CHARACTERISTICS:
        (A) LENGTH: 1135 base pairs
        (B) TYPE: nucleotide
        (C) STRANDEDNESS: double
        (D) TOPOLOGY: linear (ii) MOLECULE TYPE: genomic DNA (vi) ORIGINAL SOURCE:
        (A) ORGANISM: Escherichia coli
        (B) STRAIN: W3110

(vii) IMMEDIATE SOURCE:
        (B) CLONE: pPC43

(xi) SEQUENCE DESCRIPTION: SEQ ID NO: 2:

```
TCCGCGAACT GGCGCATCGC TTCGGCGTTG AAATGCCAAT AACCGAGGAA ATTTATCAAG      60
TATTATATTG CGGAAAAAAC GCGCGCGAGG CAGCATTGAC TTTACTAGGT CGTGCACGCA     120
AGGACGAGCG CAGCAGCCAC TAACCCCAGG GAACCTTTGT TACCGCTATG ACCCGGCCCG     180
CGCAGAACGG GCCGGTCATT ATCTCATCGT GTGGAGTAAG CAATGTCGTG TGAAGAACTG     240
GAAATTGTCT GGAACAATAT TAAAGCCGAA GCCAGAACGC TGGCGGACTG TGAGCCAATG     300
CTGGCCAGTT TTTACCACGC GACGCTACTC AAGCACGAAA ACCTTGGCAG TGCACTGAGC     360
TACATGCTGG CGAACAAGCT GTCATCGCCA ATTATGCCTG CTATTGCTAT CCGTGAAGTG     420
GTGGAAGAAG CCTACGCCGC TGACCCGGAA ATGATCGCCT CTGCGGCCTG TGATATTCAG     480
GCGGTGCGTA CCCGCGACCC GGCAGTCGAT AAATACTCAA CCCCGTTGTT ATACCTGAAG     540
GGTTTTCATG CCTTGCAGGC CTATCGCATC GGTCACTGGT TGTGGAATCA GGGGCGTCGC     600
GCACTGGCAA TCTTTCTGCA AAACCAGGTT TCTGTGACGT TCCAGGTCGA TATTCACCCG     660
GCAGCAAAAA TTGGTCGCGG TATCATGCTT GACCACGCGA CAGGCATCGT CGTTGGTGAA     720
ACGGCGGTGA TTGAAAACGA CGTATCGATT CTGCAATCTG TGACGCTTGG CGGTACGGGT     780
AAATCTGGTG GTGACCGTCA CCCGAAAATT CGTGAAGGTG TGATGATTGG CGCGGGCGCG     840
AAAATCCTCG GCAATATTGA AGTTGGGCGC GGCGCGAAGA TTGGCGCAGG TTCCGTGGTG     900
CTGCAACCGG TGCCGCCGCA TACCACCGCC GCTGGCGTTC CGGCTCGTAT TGTCGGTAAA     960
CCAGACAGCG ATAAGCCATC AATGGATATG GACCAGCATT TCAACGGTAT TAACCATACA    1020
TTTGAGTATG GGGATGGGAT CTAATGTCCT GTGATCGTGC CGGATGCGAT GTAATCATCT    1080
ATCCGGCCTA CAGTAACTAA TCTCTCAATA CCGCTCCCGG ATACCCCAAC TGTCG         1135
```

(2) INFORMATION FOR SEQ ID NO: 3:

(i) SEQUENCE CHARACTERISTICS:
        (A) LENGTH: 42 base pairs
        (B) TYPE: nucleotide
        (C) STRANDEDNESS: single
        (D) TOPOLOGY: linear (ii) MOLECULE TYPE: miscellaneous nucleic acid
        (A) DESCRIPTION: /desc = "oligonucleotide"

(vii) IMMEDIATE SOURCE:

(A) LIBRARY: synthetic
        (B) CLONE: cysE-fw1

(xi) SEQUENCE DESCRIPTION: SEQ ID NO: 3:

GCCTGGATCC TGCAGTCGAC CTGGCGCATC GCTTCGGCGT TG                42

(2) INFORMATION FOR SEQ ID NO: 4:

(i) SEQUENCE CHARACTERISTICS:
        (A) LENGTH: 41 base pairs
        (B) TYPE: nucleotide
        (C) STRANDEDNESS: single
        (D) TOPOLOGY: linear (ii) MOLECULE TYPE: miscellaneous nucleic acid
        (A) DESCRIPTION: /desc = "oligonucleotide"

(vii) IMMEDIATE SOURCE:
        (A) LIBRARY: synthetic
        (B) CLONE: cysE-rev1

(xi) SEQUENCE DESCRIPTION: SEQ ID NO: 4:

GTAGGAGCTC TGCAGAATTC GGGTATCCGG GAGCGGTATT G                 41

(2) INFORMATION FOR SEQ ID NO: 5:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: miscellaneous nucleic acid
        (A) DESCRIPTION: /desc = "oligonucleotide"

(vii) IMMEDIATE SOURCE:
        (A) LIBRARY: synthetic
        (B) CLONE: cysE-Mut-1

(xi) SEQUENCE DESCRIPTION: SEQ ID NO: 5:

GCCGCTAGCG TTCCGGCT                                           18

(2) INFORMATION FOR SEQ ID NO: 6:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: miscellaneous nucleic acid
        (A) DESCRIPTION: /desc = "oligonucleotide"

(vii) IMMEDIATE SOURCE:
        (A) LIBRARY: synthetic
        (B) CLONE: cysE-Mut-3

(xi) SEQUENCE DESCRIPTION: SEQ ID NO: 6:

CCGCCGCATA CCACCGCCGT T                                       21

(2) INFORMATION FOR SEQ ID NO: 7:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: miscellaneous nucleic acid
        (A) DESCRIPTION: /desc = "oligonucleotide"

(vii) IMMEDIATE SOURCE:
              (A) LIBRARY: synthetic
              (B) CLONE: cysE-Mut-6

(xi) SEQUENCE DESCRIPTION: SEQ ID NO: 7:

CCATCAATGG ATATAGACCA GCAT                                              24

(2) INFORMATION FOR SEQ ID NO: 8:

(i) SEQUENCE CHARACTERISTICS:
              (A) LENGTH: 24 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-Mut-10

(xi) SEQUENCE DESCRIPTION: SEQ ID NO: 8:

GTCGTTGGTG AAGCGGCGGT GATT                                              24

(2) INFORMATION FOR SEQ ID NO: 9:

(i) SEQUENCE CHARACTERISTICS:
              (A) LENGTH: 38 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-LHfw1

(xi) SEQUENCE DESCRIPTION: SEQ ID NO: 9:

TGGACCAGAG CTCTGGCTGG CGCATCGCTT CGGCGTTG                               38

(2) INFORMATION FOR SEQ ID NO: 10:

(i) SEQUENCE CHARACTERISTICS:
              (A) LENGTH: 46 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-Del270

(xi) SEQUENCE DESCRIPTION: SEQ ID NO: 10:

CTCGATGCAT TACGTATTAC CCATACTCAA ATCTATGGTT AATACC                      46

(2) INFORMATION FOR SEQ ID NO: 11:

(i) SEQUENCE CHARACTERISTICS:
              (A) LENGTH: 46 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-Del268

(xi) SEQUENCE DESCRIPTION: SEQ ID NO: 11:

CTCGATGCAT TACGTATTAC TCAAATGTAT GGTTAATACC GTTGAA                    46

(2) INFORMATION FOR SEQ ID NO: 12:

(i) SEQUENCE CHARACTERISTICS:
              (A) LENGTH: 46 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-Del263

(xi) SEQUENCE DESCRIPTION: SEQ ID NO: 12:

CTCGATGCAT TACGTATTAA ATACCGTTGA AATGCTGGTC CATATC                    46

(2) INFORMATION FOR SEQ ID NO: 13:

(i) SEQUENCE CHARACTERISTICS:
              (A) LENGTH: 46 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-Del259

(xi) SEQUENCE DESCRIPTION: SEQ ID NO: 13:

CTCGATGCAT TACGTATTAA TGCTGGTCCA TATCCATTGA TGGCTT                    46

(2) INFORMATION FOR SEQ ID NO: 14:

(i) SEQUENCE CHARACTERISTICS:
              (A) LENGTH: 46 base pairs
              (B) TYPE: nucleotide
              (C) STRANDEDNESS: single
              (D) TOPOLOGY: linear (ii) MOLECULE TYPE: miscellaneous nucleic acid
              (A) DESCRIPTION: /desc = "oligonucleotide"

(vii) IMMEDIATE SOURCE:
              (A) LIBRARY: synthetic
              (B) CLONE: cysE-Del258

(xi) SEQUENCE DESCRIPTION: SEQ ID NO: 14:

CTCGATGCAT TACGTATTAC TGGTCCATAT CCATTGATGG CTTATC                    46

(2) INFORMATION FOR SEQ ID NO: 15:

(i) SEQUENCE CHARACTERISTICS:
              (A) LENGTH: 47 base pairs
              (B) TYPE: nucleotide
              (C) STRANDEDNESS: single
              (D) TOPOLOGY: linear (ii) MOLECULE TYPE: miscellaneous nucleic acid (A) DESCRIPTION: /desc = "oligonucleotide"

(vii) IMMEDIATE SOURCE:
                (A) LIBRARY: synthetic
                (B) CLONE: cysE-Del257

(xi) SEQUENCE DESCRIPTION: SEQ ID NO: 15:

CTCGATGCAT TACGTATTAG TCCATATCCA TTGATGGCTT ATCGCTG                    47

(2) INFORMATION FOR SEQ ID NO: 16:

(i) SEQUENCE CHARACTERISTICS:
                (A) LENGTH: 46 base pairs
                (B) TYPE: nucleotide
                (C) STRANDEDNESS: single
                (D) TOPOLOGY: linear (ii) MOLECULE TYPE: miscellaneous nucleic acid
                (A) DESCRIPTION: /desc = "oligonucleotide"

(vii) IMMEDIATE SOURCE:
                (A) LIBRARY: synthetic
                (B) CLONE: cysE-Del256

(xi) SEQUENCE DESCRIPTION: SEQ ID NO: 16:

CTCGATGCAT TACGTATTAC ATATCCATTG ATGGCTTATC GCTGTC                    46

(2) INFORMATION FOR SEQ ID NO: 17:

(i) SEQUENCE CHARACTERISTICS:
                (A) LENGTH: 46 base pairs
                (B) TYPE: nucleotide
                (C) STRANDEDNESS: single
                (D) TOPOLOGY: linear (ii) MOLECULE TYPE: miscellaneous nucleic acid
                (A) DESCRIPTION: /desc = "oligonucleotide"

(vii) IMMEDIATE SOURCE:
                (A) LIBRARY: synthetic
                (B) CLONE: cysE-Del255

(xi) SEQUENCE DESCRIPTION: SEQ ID NO: 17:

CTCGATGCAT TACGTATTAA TCCATTGATG GCTTATCGCT GTCTGG                    46

(2) INFORMATION FOR SEQ ID NO: 18:

(i) SEQUENCE CHARACTERISTICS:
                (A) LENGTH: 46 base pairs
                (B) TYPE: nucleotide
                (C) STRANDEDNESS: single
                (D) TOPOLOGY: linear (ii) MOLECULE TYPE: miscellaneous nucleic acid
                (A) DESCRIPTION: /desc = "oligonucleotide"

(vii) IMMEDIATE SOURCE:
                (A) LIBRARY: synthetic
                (B) CLONE: cysE-Del250

(xi) SEQUENCE DESCRIPTION: SEQ ID NO: 18:

CTCGATGCAT TACGTATTAA TCGCTGTCTG GTTTACCGAC AATACG                    46

(2) INFORMATION FOR SEQ ID NO: 19:

(i) SEQUENCE CHARACTERISTICS:
                (A) LENGTH: 46 Base pairs
                (B) TYPE: nucleotide
                (C) STRANDEDNESS: single
                (D) TOPOLOGY: linear

```
        (ii) MOLECULE TYPE: miscellaneous nucleic acid:
            (A) DESCRIPTION: /desc = "oligonucleotide"

(vii) IMMEDIATE SOURCE:
            (A) LIBRARY: synthetic
            (B) CLONE: cysE-Del249

(xi) SEQUENCE DESCRIPTION: SEQ ID NO: 19:

CTCGATGCAT TACGTATTAG CTGTCTGGTT TACCGACAAT ACGAGC                46

(2) INFORMATION FOR SEQ ID NO: 20:

(i) SEQUENCE CHARACTERISTICS:
            (A) LENGTH: 46 base pairs
            (B) TYPE: nucleotide
            (C) STRANDEDNESS: single
            (D) TOPOLOGY: linear (ii) MOLECULE TYPE: miscellaneous nucleic acid
            (A) DESCRIPTION: /desc = "oligonucleotide"

(vii) IMMEDIATE SOURCE:
            (A) LIBRARY: synthetic
            (B) CLONE: cysE-Del248

(xi) SEQUENCE DESCRIPTION: SEQ ID NO: 20:

CTCGATGCAT TACGTATTAG TCTGGTTTAC CGACAATACG AGCCGG                46

(2) INFORMATION FOR SEQ ID NO: 21:

(i) SEQUENCE CHARACTERISTICS:
            (A) LENGTH: 46 base pairs
            (B) TYPE: nucleotide
            (C) STRANDEDNESS: single
            (D) TOPOLOGY: linear (ii) MOLECULE TYPE: miscellaneous nucleic acid
            (A) DESCRIPTION: /desc = "oligonucleotide"

(vii) IMMEDIATE SOURCE:
            (A) LIBRARY: synthetic
            (B) CLONE: cysE-Del245

(xi) SEQUENCE DESCRIPTION: SEQ ID NO: 21:

CTCGATGCAT TACGTATTAA CCGACAATAC GAGCCGGAAC GCCAGC                46

(2) INFORMATION FOR SEQ ID NO: 22:

(i) SEQUENCE CHARACTERISTICS:
            (A) LENGTH: 46 base pairs
            (B) TYPE: nucleotide
            (C) STRANDEDNESS: single
            (D) TOPOLOGY: linear (ii) MOLECULE TYPE: miscellaneous nucleic acid
            (A) DESCRIPTION: /desc = "oligonucleotide"

(vii) IMMEDIATE SOURCE:
            (A) LIBRARY: synthetic
            (B) CLONE: cysE-Del239

(xi) SEQUENCE DESCRIPTION: SEQ ID NO: 22:

CTCGATGCAT TACGTATTAA ACGCCAGCGG CGGTGGTATC CGGCGG                46

(2) INFORMATION FOR SEQ ID NO: 23:

(i) SEQUENCE CHARACTERISTICS:
            (A) LENGTH: 46 base pairs
            (B) TYPE: nucleotide
            (C) STRANDEDNESS: single
            (D) TOPOLOGY: linear
```

```
        (ii) MOLECULE TYPE:  miscellaneous nucleic acid
              (A) DESCRIPTION:  /desc = "oligonucleotide"

(vii) IMMEDIATE SOURCE:
              (A) LIBRARY: synthetic
              (B) CLONE: cysE-Del227

(xi) SEQUENCE DESCRIPTION:  SEQ ID NO: 23:

CTCGATGCAT TACGTATTAC AGCACCACGG AACCTGCGCC AATCTT                    46

(2) INFORMATION FOR SEQ ID NO: 24:

(i) SEQUENCE CHARACTERISTICS:
              (A) LENGTH: 38 base pairs
              (B) TYPE: nucleotide
              (C) STRANDEDNESS: single
              (D) TOPOLOGY: linear (ii) MOLECULE TYPE:  miscellaneous nucleic acid
              (A) DESCRIPTION:  /desc = "oligonucleotide"

(vii) IMMEDIATE SOURCE:
              (A) LIBRARY: synthetic
              (B) CLONE: cysE-LHrev1

(xi) SEQUENCE DESCRIPTION:  SEQ ID NO: 24:

CTCGATGCAT TACGTAGGGG TATCCGGGAG CGGTATTG                             38
```

PROCESS FOR PREPARING O-ACETYLSERINE, L-CYSTEINE AND L-CYSTEINE-RELATED PRODUCTS

This is a 371 of PCT/EP 96/04613 filed Oct. 24, 1996.

BACKGROUND OF THE INVENTION

1. Field of the Invention

The present invention relates to a process for preparing O-acetylserine, L-cysteine and sulfur-containing compounds derived therefrom.

2. The Prior Art

L-cysteine and its derivatives are employed in the pharmaceutical sphere (treatment of bronchial diseases), in the cosmetics sector (as constituents of hair shampoos and permanent wave lotions) and in the foodstuffs sphere (as antioxidants, as flavor enhancers and as adjuvants in the working of the dough). L-cysteine has hitherto been obtained by extraction from keratin-containing material, such as hair, bristles, horns, hooves and feathers, or by the enzymic transformation of precursors. An overproduction of L-cysteine by microorganisms is very desirable since L-cysteine is not only an economically interesting compound but, in addition, as is evident from FIGS. 1–3, constitutes an important intermediate in the synthesis of glutathione, methionine and biotin.

In all organisms, L-cysteine occupies a key position in sulfur metabolism and is used in the synthesis of proteins, glutathione, biotin, methionine and other sulfur-containing metabolites. Furthermore, L-cysteine acts as a precursor in the biosynthesis of coenzyme A; in addition to this, L-cysteine can readily be oxidized to cystine. A close connection exists between the biosynthesis of L-cysteine and that of other amino acids such as L-serine, glycine and L-methionine.

The synthesis of L-cysteine (FIG. 4) has been investigated in detail in prokaryotes, in particular bacteria (Kredich, N. M. and G. M. Tomkins 1966, J. Biol. Chem. 241: 4955–4965; Kredich, N. M., 1987, Biosynthesis of Cysteine. In: Neidhardt F. C., Ingraham, J. L., Magasanik, B., Low. K. B., Schaechter, M., Umbarger, H. E. (eds) *Escherichia coli* and *Salmonella typhimurium:* cellular and molecular biology, Vol. 1. American Society for Microbiology, Washington D.C., 419–428). The key reaction consists of the transfer of an acetyl group to serine in order to produce O-acetylserine 1), followed by the substitution of the acetyl group by the SH group, resulting in the synthesis of L-cysteine 2).

1) L-serine+acetyl-coenzyme A→O-acetylserine+coenzyme A

2) O-acetylserine+$H_2S$→L-cysteine+acetate

In microorganisms and in plants, O-acetylserine, and not serine, acts as the immediate precursor of the carbon skeleton of L-cysteine (Kredich, N. M. and G. M. Tomkins 1966, J. Biol. Chem. 241: 4955–4965). The reaction in which the acetyl group is transferred in order to produce an activated form of L-serine is catalyzed by the serine acetyltransferase (EC 2.3.1.30) which is encoded by the cysE gene and is subject to strict control by the end product L-cysteine. The gene for serine acetyltransferase has already been cloned and the amino acid sequence which is deduced from the DNA sequence is known (Denk, D. and Böck, A. 1987, J. Gen. Microbiol. 133: 515–525).

The formation of L-cysteine itself is catalyzed by two O-acetylserine sulfhydrylase isoenzymes (EC 4.2.99.8), encoded by the genes cysK (O-acetylserine sulfhydrylase A) and cysM (O-acetylserine sulfhydrylase B), a reaction in which O-acetylserine functions as a β-alanyl donor and $H_2S$ as a β-alanyl acceptor (Kredich, N. M. and G. M. Tomkins 1966, J. Biol. Chem. 241: 4955–4965), with the O-acetylserine sulfhydrylase A making the major contribution to the cysteine synthesis. In addition, O-acetylserine sulfhydrylase B (cysM) is able to utilize thiosulfate as a sulfur source (Sirko, A. et al., 1987, J. Gen. Microbiol. 133: 2719–2725). The O-acetylserine sulfhydrylase B catalyzes the reaction between O-acetylserine and thiosulfate to form S-sulfocysteine, which can then be converted to cysteine (Nakamura, T., et al, 1983, J. Bacteriol. 156, 656–662).

The end product inhibition by L-cysteine of the wild-type form of serine acetyltransferase is a physiologically important factor in the kinetic regulation of cysteine biosynthesis (Kredich, N. M. 1971, J. Biol. Chem. 246, 3474–3484; Kredich, N. M. and G. M. Tomkins 1966, J. Biol. Chem. 241, 4955–4965). The activity of the wild-type form of serine acetyltransferase is inhibited by cysteine. This inhibition has been investigated kinetically and was found to have a competitive character. An inhibitor constant $K_i=1.1 \times 10^{-6}$ M was determined in the presence of 0.1 mM acetyl-coenzyme A and 1 mM L-serine (Kredich, N. M. 1971 and Tomkins G. M. 1966, J. Biol. Chem. 241, 4955–4965).

An example is known from the literature of it being possible to isolate a cysteine-prototrophic revertant, whose serine acetyltransferase activity exhibits an end product inhibition by L-cysteine which is only weakly pronounced due to an amino acid substitution in the coding region, by chemically mutagenizing a cysteine-auxotrophic strain with ethyl methanesulfonate (Denk, D., Böck, A., 1987, J. Gen. Microbiol. 133: 515–525). According to the literature reference mentioned, the feedback resistance of this mutant is elevated 10-fold. Consequently, the $K_i$ of this mutant is approx. 0.01 mM, when comparison is made with the wild-type form.

SUMMARY OF THE INVENTION

The present invention relates to serine acetyltransferases which exhibit a sensitivity to the inhibitor L-cysteine which is reduced in comparison to the wild-type enzyme and whose protein sequence exhibits at least one mutation or deletion when compared with the wild-type sequence, wherein the mutation is in the sequence region from the amino acid in position 97 up to and including the amino acid in position 273, or the deletion is in the carboxyterminal sequence region from the amino acid in position 227 onwards, with position 1 being the start methionine in FIG. 5 (SEQ ID NO: 1) and with the protein sequence having the mutation of Met to Ile in position 256 being excluded.

It has been found, surprisingly, that the novel amino acid substitutions and/or amino acid deletions of the carboxyl terminus of the serine acetyltransferase lead to a diminution in the cysteine sensitivity while at the same time allowing adequate enzymic activity to be retained.

The novel serine acetyltransferases preferably have an inhibitor constant, $K_i$, of from 0.005 to 2.3 mM in the presence of 1 mM L-serine and 0.1 mM acetyl-CoA, where serine acetyltransferases having at least one mutation preferably possess an inhibitor constant, $K_i$, of from 0.015 to 2.3 mM in the presence of 1 mM L-serine and 0.1 mM acetyl-CoA, while serine acetyltransferases having at least one carboxyterminal deletion preferably exhibit an inhibitor constant, $K_i$, of from 0.005 to 0.03 mM in the presence of 1 mM L-serine and 0.1 mM acetyl-CoA.

The inhibitor constant ($K_i$) towards L-cysteine of the particularly preferred enzyme mutants are between 0.02 and 2.3 mM in the presence of 1 mM L-serine and 0.1 mM acetyl-CoA.

Novel serine acetyltransferases exhibit an activity which is adequate for the growth of the microorganisms which contain them.

Preferably, the protein sequence of a novel serine acetyltransferase contains the amino acid substitution of at least one of the cysE mutants specified in Tab. 1a or 1b.

found, in every case, to be at least five times more resistant to the inhibitor L-cysteine when compared with the wild-type.

The present invention furthermore relates to DNA sequences which encode novel serine acetyltransferases.

These DNA sequences are characterized by the fact that they exhibit at least one mutation in the coding DNA sequence region, from bp 510 to bp 1040, of the respective cysE gene, with bp 1 being the first base in FIG. 6 (SEQ ID NO: 2) and with the mutation of guanine to adenine in position 990 being excluded.

TABLE 1a

Feedback-resistant cysE alleles possessing single or multiple amino acid changes in the coding region

| cysE mutant | Nucleotide substitution (No.) | Amino Acid substitution (No.) | $K_i$ ($\mu$M) | spec. act. $\mu$mol/min × mg |
|---|---|---|---|---|
| cysEII | GGC—>AGC (934) | Gly238—>Ser238 | 10 | 0.068 |
| cysEIII | GGT—>GAT (716) | Gly165—>Asp165 | 10 | 0.030 |
| cysEIV | GCT—>GTT (932) | Ala237—>Val237 | 40 | 0.170 |
|  | GGC—>AGC (934) | Gly238—>Ser238 |  |  |
| cysEV | GCT—>GTT (932) | Ala237—>Val237 |  |  |
|  | GGC—>AGC (934) | Gly238—>Ser238 | 10 | 0.246 |
|  | ATG—>ATA (990) | Met256—>Ile256 |  |  |
| cysEVI | GGC—>AGC (934) | Gly238—>Ser238 | 10 | 0.075 |
|  | ATG—>ATA (990) | Met256—>Ile256 |  |  |
| cysEVII | GCT—>GTT (932) | Ala237—>Val237 | 10 | 0.253 |
| cysEVIII | ATG—>ATA (990) | Met256—>Ile256 | 30 | 0.160 |
|  | GCT—>GTT (932) | Ala237—>Val237 |  |  |
| cysEX | ACG—>GCG (721) | Thr167—>Ala167 | 50 | 0.156 |
| cysEXI | ACG—>GCG (721) | Thr167—>Ala167 | 700 | 0.117 |
|  | GGT—>AGT (955) | Gly245—>Ser245 |  |  |
| cysEXII | AAA—>CAA (511) | Lys97—>Gln97 | 40 | 0.254 |
|  | GGC—>AGC (934) | Gly238—>Ser238 |  |  |
|  | TTT—>TTG (1023) | Phe267—>Leu267 |  |  |
| cysEXIII | GTT—>GCT (713) | Val164—>Ala164 | 30 | 0.213 |
|  | TTT—>TTG (1023) | Phe267—>Leu267 |  |  |
| cysEXIV | ACG—>GCG (721) | Thr167—>Ala167 | >1000 | 0.453 |
|  | ATG—>TAG (988 + 989) | Met256—>Stop256 |  |  |
| cysEXVI | GAT—>GGT (971) | Asp250—>Gly250 | 50 | 0.554 |
|  | AAG—>TAG (973) | Lys251—>Stop251 |  |  |
| cysEXVII | GGT—>GAT (716) | Gly165—>Asp165 | 100 | 0.052 |
|  | ACG—>GCG (721) | Thr167—>Ala167 |  |  |
| cysEXXIII | ACG—>GCG | Thr167—>Ala167 | 2300 | 0.085 |
|  | GCT—>GTT | Ala237—>Val237 |  |  |
|  | GGC—>AGC | Gly238—>Ser238 |  |  |

TABLE 1b

Feedback-resistant cysE alleles possessing carboxyterminal deletions

| cyseE mutant | Deleted amino acids | Terminal amino acid | $K_i$ ($\mu$M) | spec.act. $\mu$mol/min x mg |
|---|---|---|---|---|
| cysE-Del259 | 14 | His259 | 7.5 | 0.328 |
| cysE-Del258 | 15 | Gln258 | 5 | 0.256 |
| cysE-Del257 | 16 | Asp257 | 7.5 | 0.394 |
| cysE-Del256 | 17 | Met256 | 12.5 | 0.366 |
| cysE-Del255 | 18 | Asp255 | 30 | 0.624 |
| cysE-Del250 | 23 | Asp250 | 20 | 0.405 |
| cysE-Del249 | 24 | Ser249 | 15 | 0.420 |
| cysE-Del248 | 25 | Asp248 | 12.5 | 0.270 |

Novel cysteine-insensitive serine acetyltransferases may be obtained, for example, by expressing DNA sequences which encode novel serine acetyltransferases.

The enzyme variants which are encoded by these DNA sequences each exhibit a different sensitivity to the inhibitor L-cysteine, with, however, the serine acetyltransferase being In that which follows, the novel DNA sequences are also termed feedback-resistant cysE alleles.

These DNA sequences can be prepared, for example, by non-specific or by targeted mutagenesis methods from starting material which is described below.

Non-specific mutations within the said DNA region may be produced, for example, by chemical agents (e.g. nitrosoguanidine, ethylmethanesulfonic acid and the like) and/or by physical methods (Miller, J. H., 1972, Experiments in Molecular Genetics, Cold Spring Harbor Laboratory, USA: 113–185) and/or by PCR reactions which are carried out under particular conditions (Gibbs, R. A. 1990, Anal. Chem. 62: 1202–1214).

Methods for introducing mutations at specific positions within a DNA fragment are known and are described, for example, in the following publications: Sarkar, G., Sommer, S. S., 1990, BioTechniques 8: 404–407 describe site-specific mutagenesis using PCR; Ausubel, F. M. et al., 1987, pp. 8.01–8.3.6 Current Protocols in Molecular Biology, Greene Publishing Associates, describe methods for site-specific mutagenesis using M13 phages.

Another method of producing feedback-resistant cysE alleles consists in combining different point mutations which lead to feedback resistance, thereby giving rise to multiple mutants possessing new properties.

The DNA of the wild-type cysE gene, or a cysE gene which has been inactivated by mutation, or a cysE gene which has been mutated and which already encodes a feedback-resistant serine acetyltransferase, is preferably used as the starting material for the mutagenesis.

The cysE gene which is to be mutated may be encoded chromosomally or extrachromosomally.

The starting DNA fragment, encompassing, for example, the wild-type cysE gene, is recombined on a vector using known standard techniques for preparing recombinant DNA. By means of using the previously mentioned mutagenesis methods, one or more nucleotides in the DNA sequence are changed such that the amino acid sequence which is now encoded by the gene exhibits at least one mutation in the sequence region from position 97 up to and including the amino acid in position 273, or at least one deletion is present in the carboxyterminal sequence region starting with the amino acid in position 227, where position 1 is the initiating methionine in FIG. 5 (SEQ ID NO: 1) and where the mutation of Met to Ile in position 256 is excluded.

Using the techniques which have been described, one or more mutations which cause the encoded serine acetyltransferase to possess an amino acid sequence which leads to cysteine insensitivity can be introduced into the said DNA region of any cysE gene.

Subsequent to the mutagenesis, which has been carried out, for example, as described, the mutants having the desired phenotype are selected, for example by means of plating on to cysteine-free medium and subsequently determining the extent to which the mutated serine acetyltransferase is sensitive to cysteine.

The invention also relates to microorganisms which contain the feedback-resistant cysE alleles.

Such strains of microorganisms are characterized by the fact that they possess a cysteine metabolism which is deregulated by at least one feedback-resistant cysE allele.

Since, in principle, cysteine metabolism proceeds by way of the same metabolic route, which is known per se, in all microorganisms, and the techniques to be used for preparing the novel strains are well known, for example from standard textbooks, and applicable to all microorganisms, novel strains can be prepared from any microorganisms whatsoever.

Bacteria are preferably suitable for preparing a novel strain.

Gram-negative bacteria, in particular *E. coli*, are particularly preferably suitable.

The invention also relates to the preparation of L-cysteine, or of products which are derived from L-cysteine, by means of cultivating novel microorganisms.

The feedback-resistant cys-E alleles render it possible to abolish the control at an important biosynthetic control point, thereby amplifying the production of a large number of compounds which are situated downstream of this control point. These include, in particular, O-acetylserine, L-cysteine and L-cysteine-related products. L-cysteine-related products are all products which are derived from L-cysteine, i.e. sulfur-containing compounds which require L-cysteine for their preparation. Examples of such products are 2(R,S)-methyl-thiazolidine-2(R,S), 4(R)-dicarboxylic acid, homocysteine, methionine, biotin and glutathione.

For the purpose of expressing the altered serine acetyltransferase enzyme, the feedback-resistant cys-E alleles are transformed into a host strain using customary methods. The screening for strains possessing altered serine acetyltransferase properties is, for example, effected using the methods described below.

In order to determine the extent of the cysteine insensitivity of the altered enzyme, the secretion of cysteine by the strain is first of all measured in a semiquantitative, so-called cross-feeding test. For this purpose, the strains to be tested are applied to cysteine-free minimal medium to which an indicator strain which is auxotrophic for cysteine has been added. The zone of growth of the indicator strain around the particular inoculation streak (halo) serves as a semiquantitative measure of the cysteine secretion. All the strains which have a halo with a radius of >2 mm in the cross-feeding test are designated as being "positive in the cross-feeding test". An enzyme activity test is carried out on the selected strains in order to determine the extent of the cysteine tolerance of the altered serine acetyltransferase.

Any method which enables the activity of the serine acetyltransferase to be determined in the presence of cysteine can be used for determining the cysteine sensitivity of this enzyme. For example, the serine acetyltransferase activity can be determined using the method described by Kredich and Tomkins, J. Biol. Chem. 241: 4955–4965 (1966). In this test, the enzyme test mixture contains the substrate, L-serine, and the cofactor, acetyl-coenzyme A. The reaction is started by adding enzyme and monitored, in a spectro photometer, by observing the decrease in absorption at 232 nm which is elicited by the cleavage of the thioester bond in the acetyl-coenzyme A.

The above-described enzyme test is suitable for determining the cysteine sensitivity of any serine acetyltransferase enzyme, including the enzymes which have a modified carboxyl terminus. Inhibition of the serine acetyltransferase activity is tested in the presence of differing concentrations of L-cysteine in the reaction mixture. The catalytic activity of the different serine acetyltransferase enzymes is determined in the presence and absence of L-cysteine, and the inhibitor constant, $K_i$, is ascertained from this (Kredich and Tomkins, J. Biol. Chem., 241, 4955–4965 (1966)).

In most cases, an enzymatically active serine acetyltransferase is preferred which has a diminished cysteine sensitivity. For other purposes, a concomitant reduction in end product sensitivity and in catalytic activity can be desirable.

As a rule, it is not desirable for an end product-resistant serine acetyltransferase to be greatly overexpressed since the O-acetylserine or L-cysteine, or the metabolites which are derivated therefrom, which are formed to too great an extent under these circumstances accumulate in the cell and toxify it and may elicit a selection of mutants which have a reduced serine acetyltransferase activity. For this reason, the feedback-resistant cysE alleles are preferably integrated into the genome as single copies using customary methods.

Methods for integrating single genes in the chromosome using suitable vectors are state of the art (e.g. Winans et al., 1985; J. Bacteriol. 161: 1219–1221; Shevell et al., 1988; J. Bacteriol. 170: 3294–3296; Kulakauskas et al. 1991, J. Bacteriol. 173: 2633–2638).

It is likewise preferred to express the feed back-resistant serine acetyltransferases on low copy number plasmids.

As is well known, the expression vector preferably possesses additional elements, which are described below, in addition to the feedback-resistant cys-E allele.

The coding sequences which are present on the vector are advantageously linked to regulatory elements which are required for expressing the coding sequences to the desired extent.

Examples of these regulatory elements are promoters, ribosomal binding sites and termination sequences. In most cases, the native, regulatory cysE sequences are used for expressing the novel mutants. However, any other regulatory sequences may also be employed.

Sequences which encode selective markers and/or reporter genes are also preferably present on the expression vector in addition to the regulatory elements. The expression of such selection markers facilitates the identification of transformants. Suitable selection markers are genes which encode resistance to, for example, ampicillin, tetracycline, kanamycin, chloramphenicol or other antibiotics.

If the novel mutant is to be replicated extrachromosomally, the plasmid vector should preferably contain an origin of replication. Strategies for integrating genes into the chromosome using vectors whose origins of replication have been removed are state of the art (Winans et al., 1985; J. Bacteriol. 161: 1219–1221; Shevell et al., 1988; J. Bacteriol. 170: 3294–3296; Kulakauskas et al. 1991, J. Bacteriol. 173: 2633–2638).

Examples of vectors which are able to replicate autonomously in *E. coli* are given in Pouwels, P. H., Enger-Valk, B. E., Brammer, W. J. 1985, Cloning Vectors, Elsevier, Amsterdam.

Examples of such vectors are:

high copy number plasmids, such as pBR322 and pUC18, medium to low copy number plasmids, such as pACYC184, pACYC177 and pSC101 phage vectors, such as M13 vectors.

Suitable, preferred vectors are those having a medium to low copy number; suitable vectors which are particularly preferred are those having a p15A replicon, such as pACYC184 (ATCC37033) or pACYC177 (ATCC37031).

A large number of vectors are also described in the literature for other bacteria (Pouwels, P. H., Enger-Valk, B. E., Brammer, W. J. 1985, Cloning Vectors, Elsevier, Amsterdam). When these vectors are used, it is possible to express the novel mutants in other bacteria.

Suitable recombinant vectors may be produced using the standard techniques for preparing recombinant DNA. These techniques are described in detail in standard textbooks.

A suitable host strain is transformed with an expression vector which contains the transcription unit encoding a cysteine-insensitive serine acetyltransferase.

Strains which contain cysteine-sensitive proteins, for example prokaryotes or yeasts, are used as host strains.

Preferably, use is made of *E. coli* wild-type strains or strains in which the endogenous cysE gene is inactivated and complemented by a novel cysE gene. Such cell systems are suitable for overproducing L-cysteine and metabolites derived from it.

When strains which contain at least one feedback-resistant cysE allele are cultured, it is found that the strains which harbor a feedback-resistant cysE allele having a $K_i$ value of between 0.015 and 2.3 mM in the presence of 1 mM L-serine and 0.1 mM acetyl-CoA secrete significantly greater quantities of cysteine.

Novel serine acetyltransferases can also be produced using antisense RNA. It is part of the state of the art to block or modify gene activity in a specific manner by means of so-called reverse genetics using antisense RNA (Inouye, 1988, Gene 72: 25–34). Antisense RNA is the transcription product of the DNA strand which is complementary to the strand encoding the protein. It is possible to reduce the cysteine sensitivity of the serine acetyltransferase in vivo by producing, by way of expression vectors, antisense RNAs which are complementary to a defined region of the 3' coding strand of the native or transformed cysE gene. In this case, the antisense RNA anneals specifically to target sequences in the cysE-mRNA and thereby elicits the synthesis of novel serine acetyltransferase enzymes which are truncated at the carboxyl terminus and, in analogy with the deletion mutants of Example 3, exhibit a diminished sensitivity towards the inhibitor L-cysteine.

An additional object was to provide sulfur sources which are suitable for ensuring optimum overproduction of cysteine by the novel microorganisms.

It has been found, surprisingly, that intracellular overproduction of O-acetylserine, which overproduction is provoked by using the novel serine acetyltransferase mutants in combination with a suitable nutrient medium, leads to a marked rise in the extracellular concentration of cysteine. Accordingly, the novel serine acetyltransferase mutants are suitable for overproducing cysteine.

In order to be able to do this, a novel microorganism must be provided with an adequate quantity of sulfur donors in the production medium.

All organic sulfur compounds are suitable for use as sulfur donors for achieving cysteine overproduction. Those which are suitable and preferred are sulfates, sulfites, sulfides, dithionites and thiosulfates. Thiosulfate is suitable and particularly preferred for achieving optimum cysteine production.

A further increase in the cysteine yield can be achieved by additionally overexpressing the sulfate-reducing enzymes (encoded by the genes cysD, C, H, G, I and J) and the sulfhydrating enzymes (encoded by the genes cysK and cysM).

A further increase in the cysteine yield is possible a) by means of deregulating the regulatory protein cysB at the gene level with the aim of achieving constitutive expression. The cysB protein functions as a protein which has overriding control in the regulation of cysteine biosynthesis in *E. coli* (Kredich, N. M., 1987, Biosynthesis of Cysteine. In: Neidhardt F. C., Ingraham, J. L., Magasanik, B., Low. K. B., Schaechter, M., Umbarger, H. E. (eds) *Escherichia coli* and *Salmonella typhimurium:* cellular and molecular biology, Vol. 1. American Society for Microbiology, Washington D.C., 419–428).

b) by means of combining ser-A genes, which are selected from the serA wild-type group and serA genes which encode a phosphoglycerate dehydrogenase having diminished sensitivity to serine, with novel cys-E genes.

c) by means of supplying serine externally.

Preferably, the gene of the native, cysteine-sensitive serine acetyltransferase is inactivated in the host strain, thereby ensuring that it is only the cysteine-insensitive serine acetyltransferase, which has been introduced into the particular strain by transformation, which is synthesized. A large number of protocols exist for inactivating native genes in *E. coli* (Hamilton et al., 1989, J. Bacteriol. 171: 4617–4622; Russel et al., 1989, J. Bacteriol. 171: 2609–2613; Shen and Huang, 1986, Genetics 112: 441–457; Jasin and Schimmel, 1984, J. Bacteriol. 159: 783–786).

Integration into the host genome of a single copy of the gene encoding an altered serine acetyltransferase is also preferred.

Descriptions of, and references for, these techniques are to be found in the following publications: Shevell et al., 1988, J. Bacteriol. 170: 3294–3296; Kulakauskas et al., 1991, J. Bacteriol. 173: 2633–2638.

Preferably, cysE alleles of differing $K_i$'s are cloned on to a low copy number vector and transformed into the appropriate production strain.

BRIEF DESCRIPTION OF THE DRAWINGS

FIG. 5 shows the amino acid sequence of *E. coli* serine acetyltransferase.

FIG. 6 shows the DNA sequence of the *E. coli* cysE gene and the amino acid sequence of the serine acetyltransferase which is deduced from this sequence.

FIG. 10 shows a nucleotide sequence discussed on page 21 of the specification.

FIG. 11 shows a nucleotide sequence discussed on page 21 of the specification.

FIG. 12 shows four nucleotide sequences for Table 3.

FIG. 13 shows a nucleotide sequence discussed on pages 27 and 31 of the specification.

FIG. 14 shows fourteen nucleotide sequences for Table 5.

FIG. 15 shows a nucleotide sequence discussed on page 31.

DETAILED DESCRIPTION OF PREFERRED EMBODIMENTS

Figure 1:
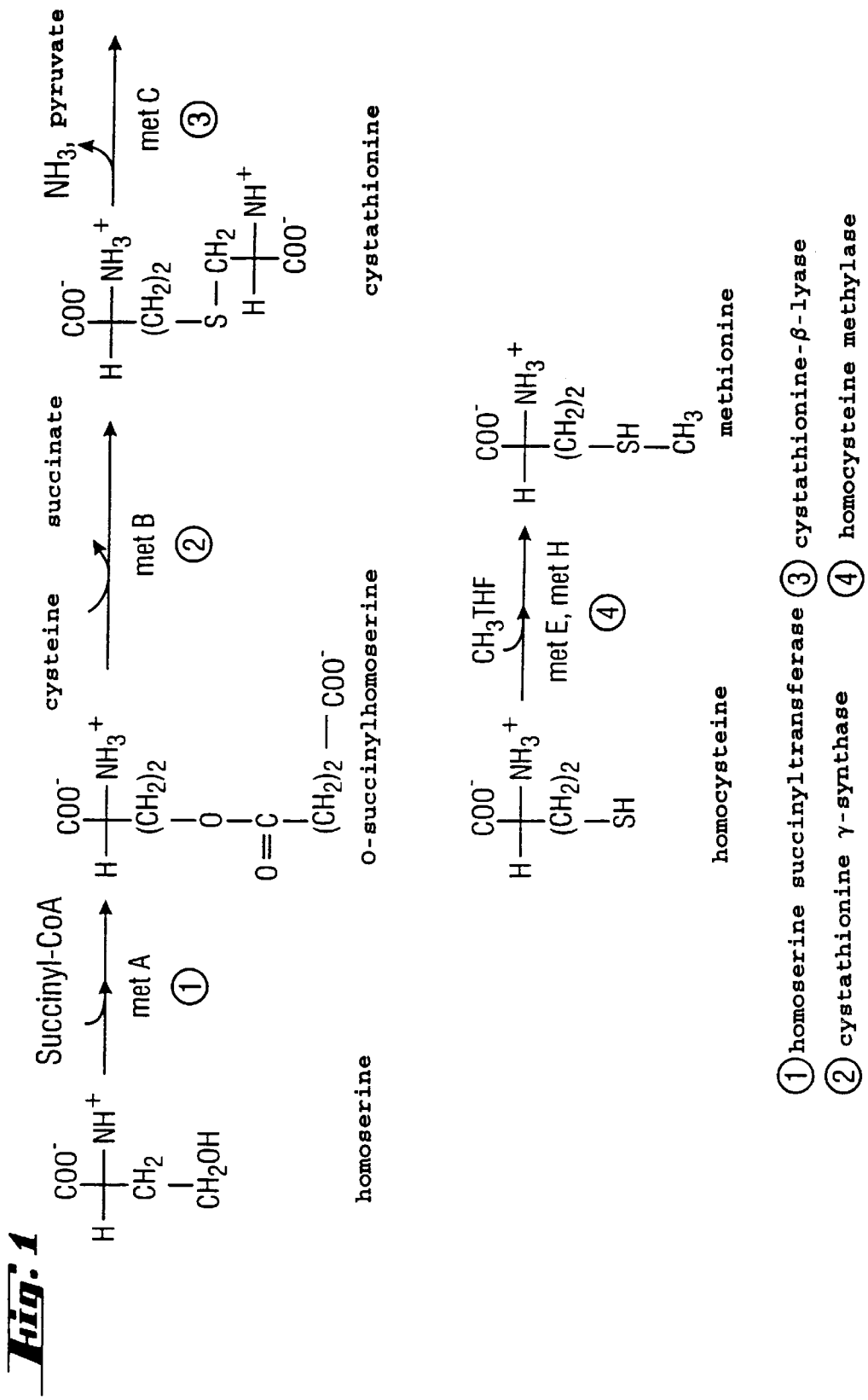
FIG. 1 shows the biosynthesis of L-methionine, starting from homoserine.
Figure 2:
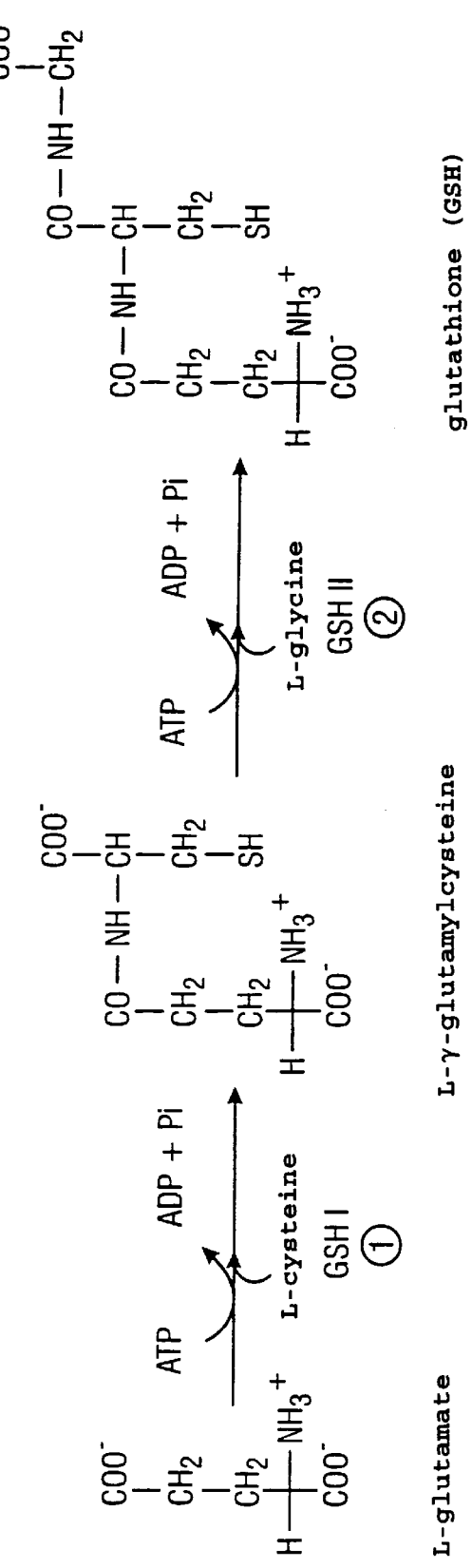
FIG. 2 shows the biosynthesis of glutathione, starting from glutamate.
Figure 3:
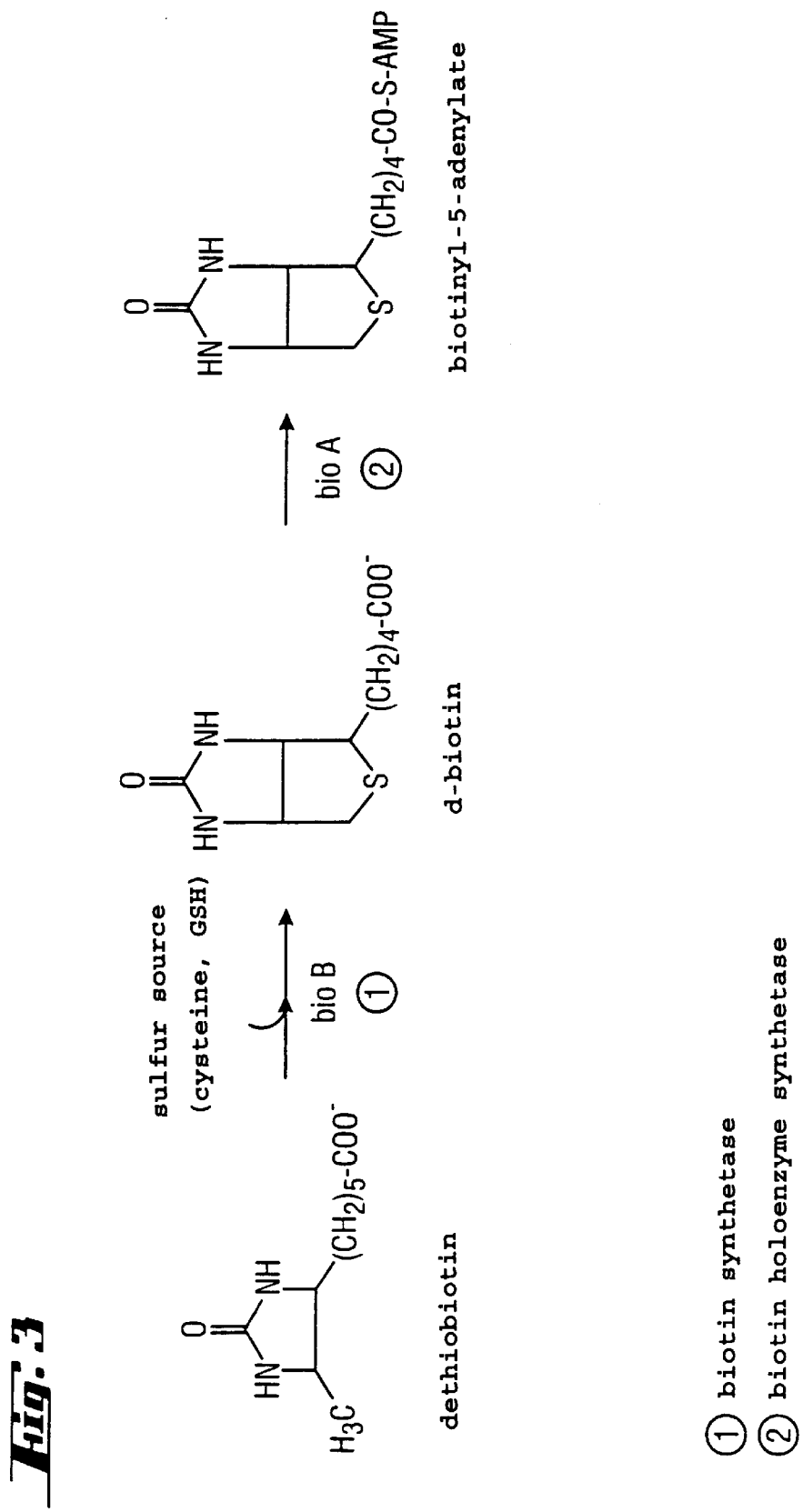
FIG. 3 shows the biosynthesis of biotin, starting from dethiobiotin.
Figure 4:
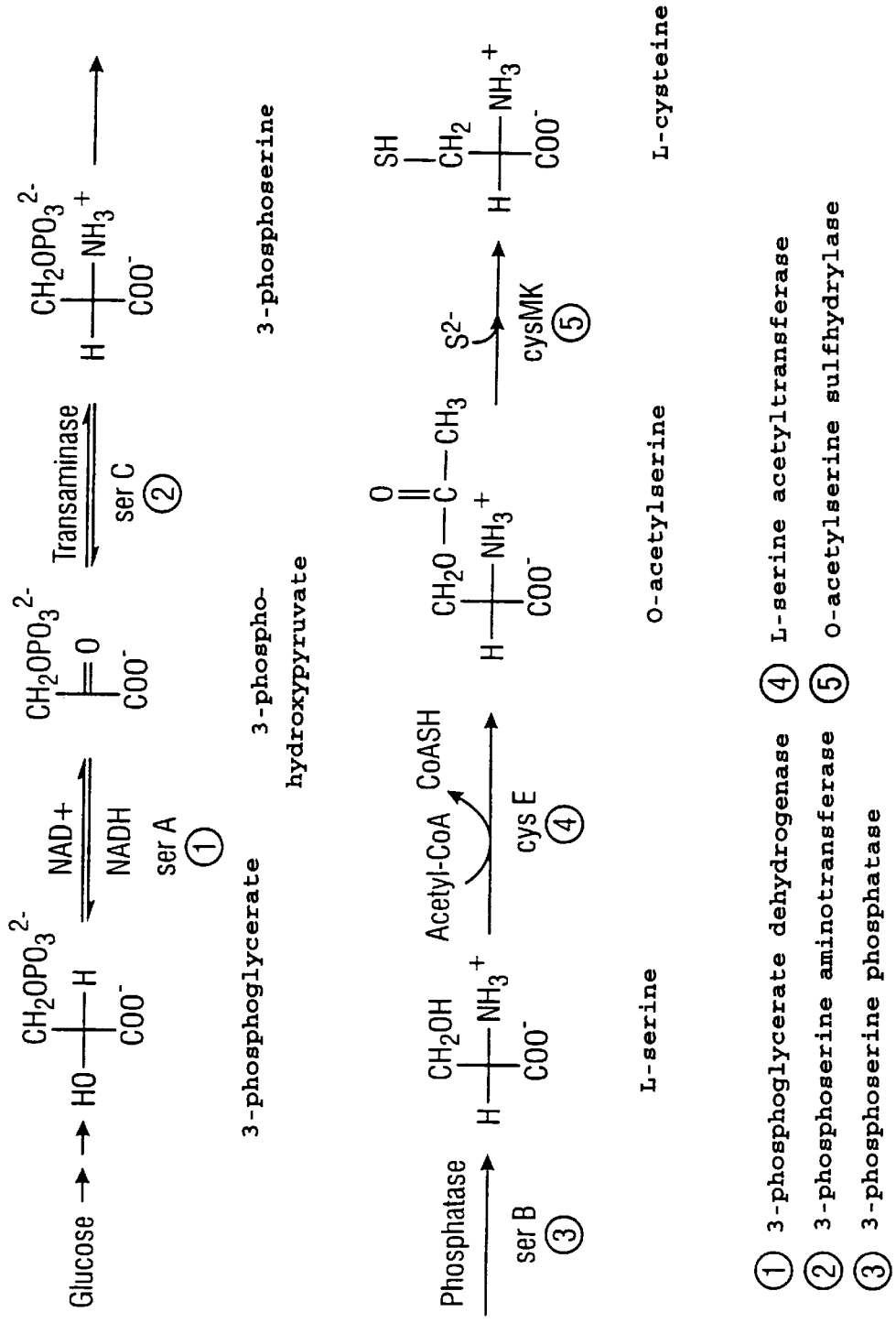
FIG. 4 shows the biosynthesis of L-cysteine in *E. coli*, starting from glucose.

The following examples serve to further clarify the invention:

EXAMPLE 1
Isolation of *E. coli* mutants containing cysteine-insensitive serine acetyltransferase enzymes It is possible to produce regulatory mutants by reverting auxotrophic *E. coli* strains. Mutants possessing the desired properties (insensitivity of the serine acetyltransferase to cysteine) are sought among the revertants of cysteine-auxotrophic cysE *E. coli* strains.

In order to isolate the revertants, use was made of the cysteine-auxotrophic *E. coli* strains JM15 (CGSC # 5042: cysE50, tfr-8), and JM39 (CGSC # 5043: cysE51, tfr-8), which strains are deposited in the Deutsche Sammlung für Mikroorganismen (German collection of microorganisms) in Braunschweig under deposition number DSM 10173. In order to produce cysteine-prototrophic revertants, these strains were treated with the mutagen nitrosoguanidine as described by Miller, J. H. (1972), *Experiments in Molecular Genetics,* Cold Spring Harbor Press: 125–129, Cold Spring Harbor Laboratory. Cysteine-prototrophic revertants were sought on cysteine-free minimal medium. Approximately 1000 of the revertants which were obtained were initially tested for cysteine secretion in the cross-feeding experiment. For this purpose, the revertants to be tested were plated on cysteine-free minimal medium (12 g/L $K_2HPO_4$, 3 g/L $KH_2PO_4$, 5 g/L $(NH_4)_2SO_4$, 0.3 g/L $MgSO_4 \times 7$ $H_2O$, 0.015 g/L $CaCl_2 \times 2$ $H_2O$, 0.002 g/L $FeSO_4 \times 7$ $H_2O$, 1 g/L $Na_3$citrate$\times 2$ $H_2O$, 0.1 g/L NaCl, 15 g/L Bacto-agar, and 1 ml/L trace element solution, consisting of 0.15 g/L $Na_2MoO_4 \times 2$ $H_2O$, 2.5 g/L $H_3BO_3$, 0.7 g/L $CoCl_2 \times 6$ $H_2O$, 0.25 g/L $CuSO_4 \times 5$ $H_2O$, 1.6 g/L $MnCl_2 \times 4$ $H_2O$, and 0.3 g/L $ZnSO_4 \times 7$ $H_2O$ (which was supplemented with 1% glucose and inoculated with $5 \times 10^6$ cells of the cysteine-auxotrophic indicator strain JM39 per ml, and incubated at 37° C. for 48 hours. The radius of the feeding auriole around the test colony (halo) was taken to be a semiquantitative measure of the cysteine secretion by the test strain. All the revertants which exhibited a growth zone larger than 2 mm were classified as being positive and isolated, and preserved, after having been streaked out several times for purification purposes.

In order to investigate the biochemical basis of the cysteine secretion of the revertants, the activity of the serine acetyltransferase was determined in vitro, and the ability of cysteine to inhibit the enzyme was measured. For the determination, use was made of S30 extracts (cell homogenates centrifuged at 30,000 g and 4° C. for 20 minutes) of the selected revertants, the starting strains and the comparison strain, *E. coli* W3110 (ATTC 27325). A number of revertants were found whose serine acetyltransferase activity still exhibited significant residual activity ($K_i$ value of between 5 and 50 $\mu$M) in the presence of differing concentrations of the inhibitor, L-cysteine.

In order to determine the ability to secrete cysteine in a liquid medium by quantitatively determining cysteine, 50 selected cysE revertants were incubated in 20 ml of standard production medium at 30° C. and at 170 rpm for a period of 48 hours. The standard production medium consisted of 15 g/L glucose, 0.08 g/L bactotryptone, 0.04 g/L yeast extract, 5 mg/L vitamin B1, 3 g/L $KH_2PO_4$, 12 g/L $K_2HPO_4$, 0.3 g/L $MgSO_4 \times 7$ $H_2O$, 0.1 g/L NaCl, 5 g/L $(NH_4)_2SO_4$, 14.7 mg/L $CaCl_2 \times 2$ $H_2O$, 2 mg/L $FeSO_4 \times 2$ $H_2O$, 1 g/L $Na_3$ citrate$\times 2$ $H_2O$, 5 g/L $Na_2S_2O_3 \times 5$ $H_2O$ and 1 ml/L trace element solution (cf. above). A sample (10 $\mu$l) was in each case removed after 24 and 48 hours and diluted, where appropriate, and the cysteine concentration in the cell-free supernatant was determined calorimetrically using the method of Gaitonde, M. K. (1967), Biochem. J. 104: 627–633. The extent of the cysteine secretion by these mutants varied from 5–60 mg/L cysteine in the culture supernatant. On the other hand, by comparison, it was not possible to detect any cysteine secretion in the *E. coli* wild-type strain. 8 revertants, whose cysteine secretion was between 40 and 60 mg/L, were selected from this screening.

In order to analyze precisely the genetic basis for the end product resistance of the serine acetyltransferases of these 8 mutants, their cysE structural genes were cloned and the DNA sequences of these genes were determined.

Since the DNA sequence of the cysE wild-type gene, and also the chromosomal restriction map of the regions flanking the cysE gene in *E. coli*, have been disclosed (Denk and Böck, 1987, J. Gen. Microbiol. 133: 515–525), it is known that the cysE structural gene is located on a 2.25 kb-sized PvuII DNA fragment.

In order to clone the cysE genes encoding the cysteine-insensitive serine acetyltransferases, the chromosomal DNA of the selected revertants was hydrolyzed completely with PvuII, the DNA hydrolysate was fractionated on a preparative agarose gel, and the DNA in the size range of 2–3 kb was isolated. The isolated PvuII hydrolysate was ligated to the SmaI-linearized and alkaline phosphatase-dephosphorylated plasmid vector pUC19 (obtainable from Boehringer Mannheim) using T4 DNA ligase.

Figure 7:
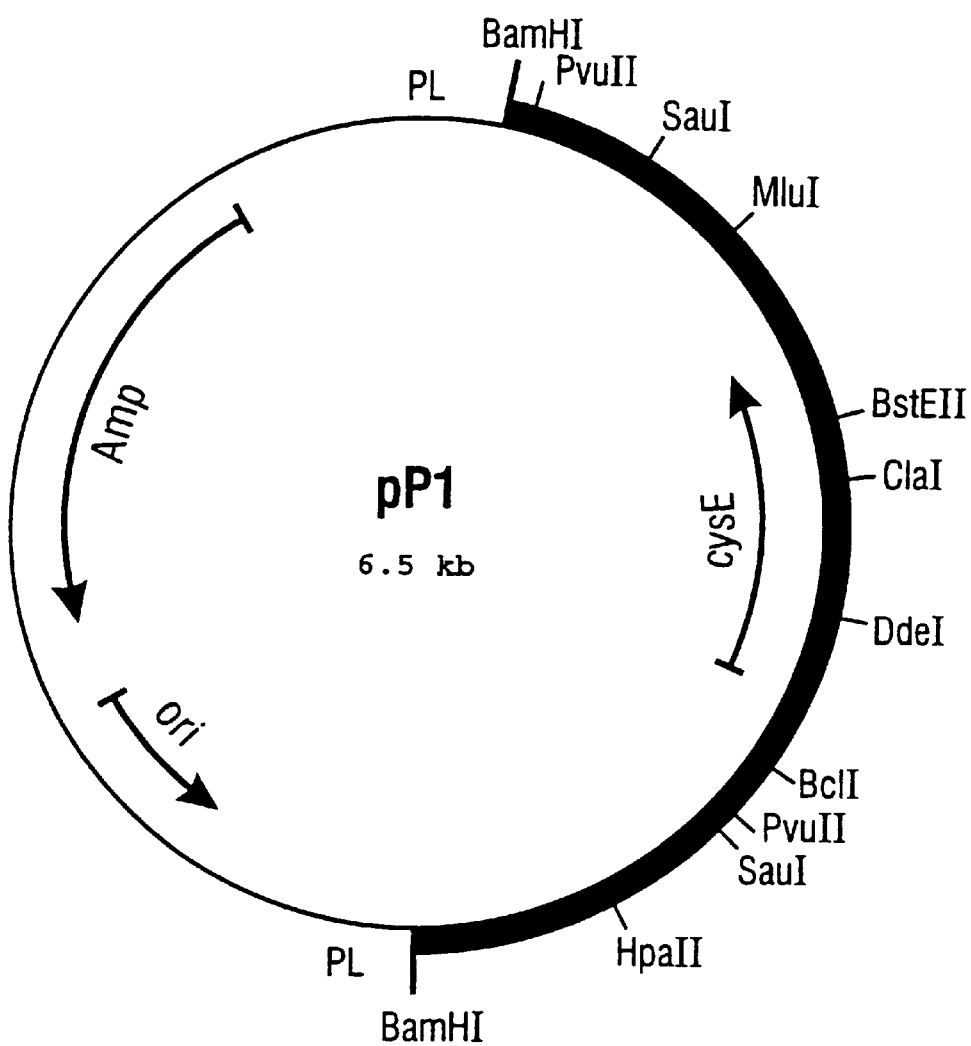
FIG. 7 shows the restriction map of the plasmid pP1 from Example 1, which plasmid contains a feedback-resistant cysE allele which is cloned, as a 2.25 kb PvuII fragment, into pUC19.

The cysteine-auxotrophic cysE strain JM15 (CGSC#5042) was transformed with the respective ligation mixture and selection was carried out on cysteine-free, ampicillin-containing (50 mg/L) minimal medium. In their restriction patterns, the plasmids (cf. FIG. 7) which were selected and which complemented the cysteine auxotrophy of the host strain exhibited the cleavage pattern which was required for the cysE gene (Denk and Böck, 1987, J. Gen. Microbiol. 133: 515–525). The selected transformants also gave rise to vigorous growth of the indicator strain JM35 (halo>4 mm) in the cross-feeding test. Determination of the activity of the serine acetyltransferase in cell extracts of these cysE mutants, which extracts were obtained by centrifuging at 30,000 g and 4° C. for 20 minutes, indicated a reduced sensitivity to L-cysteine. In order to identify exactly the changes in the structural genes of the individual cysE* alleles which led to the end product resistance, the DNA of these alleles was sequenced using cysE gene-specific oligonucleotides, and the nucleotide sequences which were found were compared with that of the cysE wild-type gene. This comparison of the nucleotide sequences gave the differences as compared with the DNA sequence and amino acid sequence of the wild-type form which are summarized in the following Table 2 (cf. FIGS. 5 and 6).

TABLE 2

Feedback-resistant cysE alleles resulting from chemical mutagenesis

| cysE mutant | nucleotide substitution (No.) | amino acid substitution (No.) | $K_i$ ($\mu M$) |
| --- | --- | --- | --- |
| cysEII | GGC->AGC (934) | Gly238->Ser238 | 10 |
| cysEIII | GGT->GAT (716) | Gly165->Asp165 | 10 |
| cysEVII | GCT->GTT (932) | Ala237->Val237 | 10 |
| cysEX | ACG->GCG (721) | Thr167->Ala167 | 50 |
| cysEXI | GGT->AGT (955) | Gly245->Ser245 | 700 |
|  | ACG->GCG (721) | Thr167->Ala167 |  |
| cysEXII | AAA->CAA (511) | Lys97->Gln97 | 40 |
|  | GGC->AGC (934) | Gly238->Ser238 |  |
|  | TTT->TTG (1023) | Phe267->Leu267 |  |
| cysEXIII | GTT->GCT (713) | Val164->Ala164 | 30 |
|  | TTT-TTG (1023) | Phe267->Leu267 |  |
| cysEXVI | GAT->GGT (971) | Asp250->Gly250 | 50 |
|  | AAG->TAG (973) | Lys251->Stop251 |  |

EXAMPLE 2

Generation of end product-insensitive serine acetyltransferases by means of specific base substitutions in the cysE structural gene In Example 1, a total of 8 different cysE alleles were described which, due to base substitutions and the accompanying amino acid changes, exhibit a substantial desensitization of the serine acetyltransferase to the L-cysteine inhibitor. These altered enzymes differ not only in the positions of the amino acid substitutions leading to the resistance but also, in some cases, in the degree of sensitivity to the L-cysteine inhibitor. End product-resistant serine acetyltransferase enzymes which possess new properties, and in which the amino acid substitutions described in Example 1 were combined with each other, were constructed by site-specific mutagenesis. The mutageneses which were required for this purpose were carried out in accordance with the state of the art using the method described by Kunkel et al. (1987), Meth. Enzymol. 154: 367–382.

Figure 8:
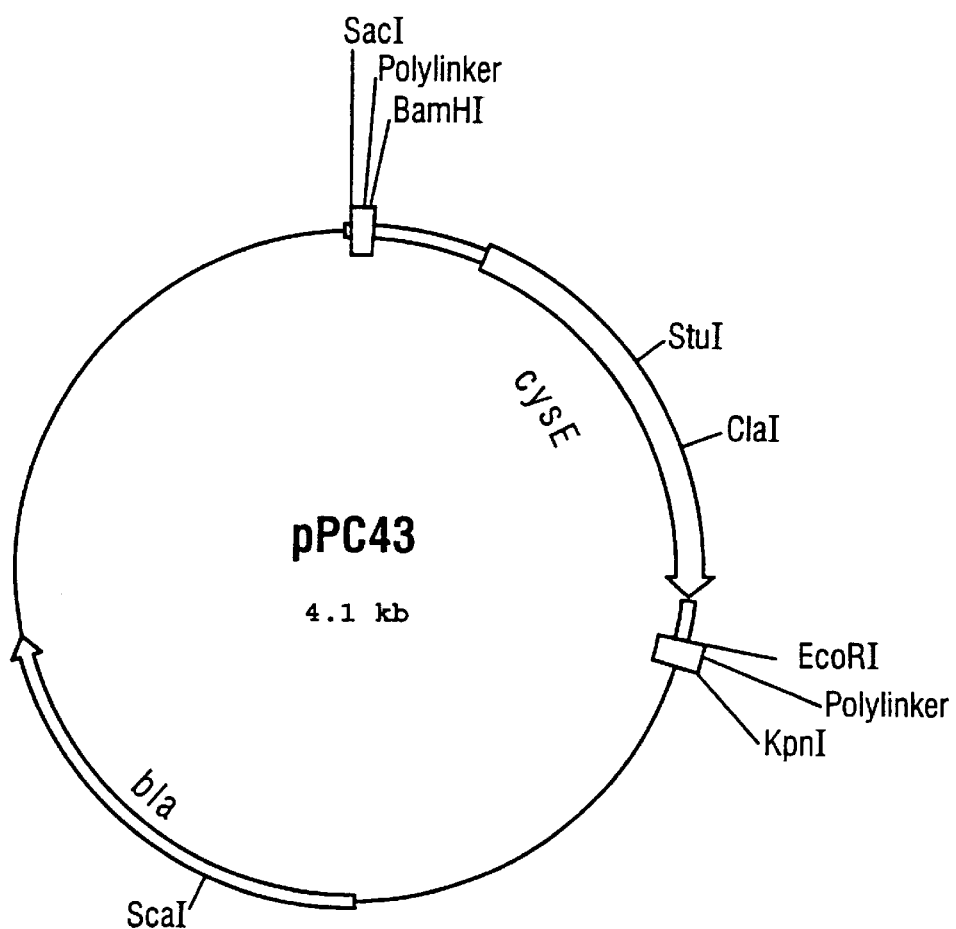
FIG. 8 shows the plasmid pPC43 from Example 2, which plasmid contains the cysE wild-type gene, as a 1.15 kb-sized EcoRI/BamHI fragment, in pBluescript.

The cysE plasmid pPC43 (deposited in the Deutsche Sammlung für Mikroorganismen, Braunschweig, under deposition number DSM 10171), which is depicted in FIG. 8 and which contains the 1.15 kb-sized cysE wild-type gene in the EcoRI-BamHI site of the phagemid vector pBluescriptII SK+ (from Stratagene, Heidelberg), was used as the starting plasmid for the mutageneses. This cysE WT gene was amplified from the genomic DNA of the E. coli wild-type strain W3110 (ATTC 27325) by means of the polymerase chain reaction (PCR) method (Saiki et al. 1988, Science 239: 487–491) using the oligonucleotide cysE-fwl (SEQ ID NO: 3) (sense primer) and cysE-revl (SEQ ID NO: 4) (antisense primer). The nucleotide sequences of these latter primers are comprised as follows:

cysE-fwl: (SEQ ID NO: 3)

This nucleotide sequence is shown in FIG. 10, wherein the moiety written in bold corresponds to bases 9–30 of the cysE DNA sequence in FIG. 6; the incorporated BamHI site is underlined.

cysE-revl: (SEQ ID NO: 4)

This nucleotide sequence is shown in FIG. 11, wherein the moiety written in bold corresponds to bases 1106–1126 of the cysE DNA sequence in FIG. 6; the incorporated EcoRI site is underlined.

The PCR experiments were carried out in 30 cycles in a thermocycler (Gene ATAQ Controller, from Pharmacia) in the presence of 200 $\mu$M deoxynucleotide triphosphates (dATP, dCTP, dGTP, dTTP), in each case 1 $\mu$M of the corresponding oligonucleotide, 100 ng of W3110 DNA, reaction buffer (10 mM Tris-HCl pH 8.3, 50 mM KCl, 1.5 mM $MgCl_2$, 0.01% gelatin) and 5 units of a heat-stable Vent DNA polymerase (from Biolabs) and under the following conditions: 96° C., 1.5 min; 62° C., 1 min; 72° C., 3 min. The amplification product was restricted with BamHI and EcoRI, purified using an agarose gel and cloned, as a 1.15 kb-sized DNA fragment, into the phagemid vector BluescriptII SK+ which had been linearized with BamHI and EcoRI, thereby resulting in the cysE plasmid pPC43 (FIG. 8).

The desired multiple mutants were made using the following procedure:

1) Preparation of the cysE IV allele: Double mutant $Val_{237}$+$Ser_{238}$

Starting with the cysE wild-type plasmid pPC43, and employing site-specific mutagenesis, a serine was initially introduced, using the mutation oligonucleotide cysE-Mut-1 (SEQ ID NO: 5) (Tab. 3), at position 238 in place of the glycine, and a valine was introduced into the resulting cysE mutant pPC34, using the mutation oligonucleotide cysE-Mut-3 (SEQ ID NO: 6) (Tab. 3), at position 237 in place of the alanine, thereby resulting in the cysE IV allele.

2) Preparation of the cysE VIII allele: Double mutant $Val_{237}$+$Ile_{256}$

Starting with the cysE wild-type plasmid pPC43, and employing site-specific mutagenesis, an isoleucine was introduced, using the mutation oligonucleotide cysE-Mut-6 (SEQ ID NO: 7) (Tab. 3), at position 256 in place of methionine, resulting in the cysE I allele. A valine was introduced, using mutation oligonucleotide cysE-Mut-3 (SEQ ID NO: 6) (Tab. 3), into this latter allele in place of the alanine at position 237. This afforded the cysE VIII allele.

3) Preparation of the CysE VI allele: Double mutant $Ser_{238}$+$Ile_{256}$

A serine was introduced, using the mutation oligonucleotide cysE-Mut-1 (SEQ ID NO: 5) (Tab. 3), into the cysE I allele (mutant $Ile_{256}$) at position 238 in place of the glycine, thereby resulting in the cysE VI allele.

4) Preparation of the cysE V allele: Triple mutant $Val_{237}$+ $Ser_{238}$+$Ile_{256}$ The methionine at position 256 in the cysE IV allele (double mutant $Val_{237}$+$Ser_{238}$) was replaced by an isoleucine using the mutation oligonucleotide cysE-Mut-6 (SEQ ID NO: 7) (Tab. 3). This afforded the cysE V allele.

5) Preparation of the cysE XIV allele: Double mutant $Ala_{167}$+$Stop_{251}$

Starting with the cysE-Del255 allele (cf. Example 3), an alanine was introduced, using the mutation oligonucleotide cysE-Mut-10 (SEQ ID NO: 8) (Tab. 3), at position 167 in place of the threonine, thereby resulting in the cysE XIV allele.

6) Preparation of the cysE XVII allele: Double mutant $ASP_{165}$+$Ala_{167}$

Starting from the cysE III allele (mutant $Asp_{165}$, cf. Example 1), the amino acid threonine at position 167 was replaced by an alanine using the oligonucleotide cysE-Mut-10 (SEQ ID NO: 8) (Tab. 3). This afforded the cysE XVII allele.

7) Preparation of the cysE XXIII allele: Triple mutant $Ala_{167}$+$Val_{237}$+$Ser_{238}$ An alanine was introduced, using the mutation oligonucleotide cysE-Mut-10 (SEQ ID NO: 8) (Tab. 3), into the cysE IV allele (double mutant $Val_{237}$+$Ser_{238}$) at position 167 instead of the threonine, thereby resulting in the cysE XXIII allele. DNA sequence analysis of the entire structural gene of the particular mutant was used to check that the mutations had been introduced correctly. An overview of the cysE* multiple mutants is presented in Tab. 4.

The biochemical parameters such as enzyme activity and inhibitor constant, $K_i$, were determined in an analogous manner to that described in Example 1.

EXAMPLE 3

Generation of end product-insensitive serine acetyltransferases by truncating the carboxyl terminus of the enzyme in a controlled manner using PCR Specific changes of one or more amino acids within a protein are state of the art and can be readily carried out at the DNA level by means of PCR technology (Saiki et al., 1988, Science 239: 487–491) using suitable mutation primers. The resulting PCR products are cloned into a suitable plasmid/host system so that the altered proteins can be expressed.

cysE mutants possessing carboxyterminal deletions of differing length, which mutants are compiled in Tab. 6, were prepared from the genomic DNA of the E. coli wild-type strain W3110 (ATTC 27325) using the oligonucleotide primers depicted in Tab. 5.

The PCR experiments were carried out in 30 cycles in a thermocycler (gene ATAQ controller, from Pharmacia) in the presence of 200 $\mu$M deoxynucleotide triphosphates (dATP, dCTP, dGTP and dTTP), in each case 1 $\mu$M of the oligonucleotides of the sense primer cysE-LHfw1 (SEQ ID NO: 9) and the corresponding antisense primer (SEQ ID NO: 10–23) (Tab. 5), 100 ng of W3110 DNA, reaction buffer (10 mM Tris-HCl pH 8.3, 50 mM KCl, 1.5 mM $MgCl_2$, 0.01% gelatin) and 5 units of a heat-stable Vent DNA polymerase (from Biolabs) and under the following conditions: 96° C., 1.5 min; 62° C., 1 min; 72° C., 3 min.

cysE-LHfw1 (SEQ ID NO: 9)

This nucleotide sequence is shown in FIG. 13.

The moiety written in bold corresponds to bases 9–30 of the cysE sequence in FIG. 6; the incorporated BstXI/SacI site is underlined.

The product which resulted after the amplification was restricted with the enzymes SacI and NsiI and then purified through an agarose gel, and the cysE DNA fragment which was isolated in each case was ligated into vector pACYC184-LH/DSM 10172) (cf. FIG. 9) which had been linearized with SacI and NsiI. Each ligation mixture was transformed into the cysteine-auxotrophic cysE strain JM15

TABLE 3

Oligonucleotides which were used for the site-specific mutation for generating new feedback-resistant cysE alleles

| SEQ ID NO: | Mutation oligo-nucleotides | Nucleotide sequence | Position in FIG. 6 | Amino acid substitution |
|---|---|---|---|---|
| 5 | cysE-Mut-1 | These four sequences are shown in FIG. 12. | 928–945 | Gly238—>Ser238 |
| 6 | cysE-Mut-3 | | 913–933 | Ala237—>Val237 |
| 7 | cysE-Mut-6 | | 976–999 | Met256—>Ile256 |
| 8 | cysE-Mut-10 | | 709–732 | Thr167—>Ala167 |

TABLE 4

Feedback-resistant cysE alleles produced by targeted site-specific mutagenesis

| cysE mutant | Nucleotide substitution (No.) | Amino acid substitution (No.) | $K_i$ ($\mu$M) |
|---|---|---|---|
| cysEIV | GCT->CTT (932) | Ala237->Val237 | 40 |
|  | GGC->AGC (934) | Gly238->Ser238 |  |
| cysEV | GCT->GTT (932) | Ala237->Val237 | 10 |
|  | GGC->AGC (934) | Gly238->Ser238 |  |
|  | ATG->ATA (990) | Met256->Ile256 |  |
| cysEVI | GGC->AGC (934) | Gly238->Ser238 | 10 |
|  | ATG->ATA (990) | Met256->Ile256 |  |
| cysEVIII | GCT->GTT (932) | Ala237->Val237 | 30 |
|  | ATG->ATA (990) | Met256->Ile256 |  |
| cysEXIV | ACG->GCG (721) | Thr167->Ala167 | >1000 |
|  | ATG->TAG (988 + 989) | Met256->stop256 |  |
| cysEXVII | GGT->GAT (716) | Gly165->Asp165 | 100 |
|  | ACG->GCG (721) | Thr167->Ala167 |  |
| cysEXXIII | ACG->GCG (721) | Thr167->Ala167 | 2300 |
|  | GCT->GTT (932) | Ala237->Val237 |  |
|  | GGC->AGC (934) | Gly238->Ser238 |  |

(CGSC#5042) and selection was carried out on cysteine-free tetracycline-containing (20 mg/l) minimal medium.

Figure 9:
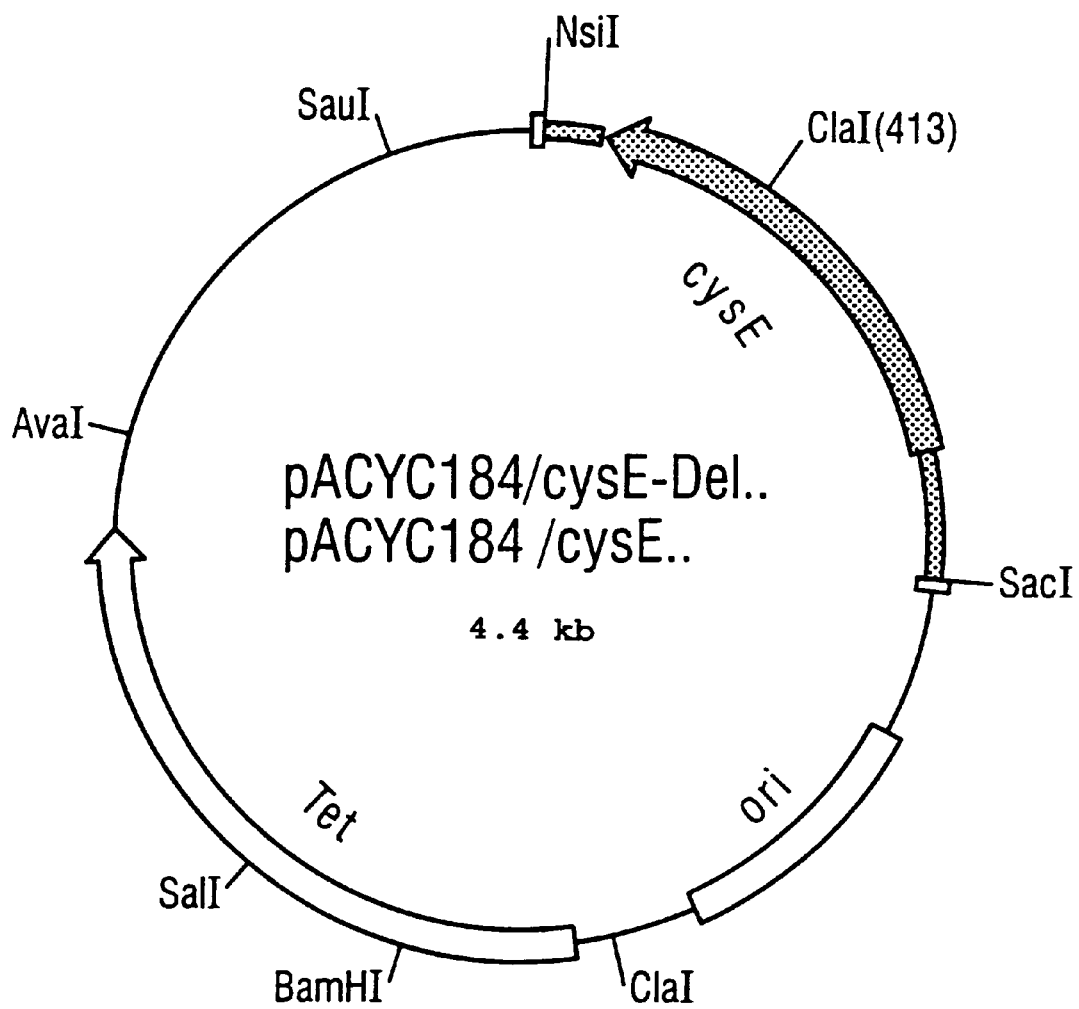
FIG. 9 shows the plasmid map of pACYC184-LH from Example 3, which plasmid contains a feedback-resistant cysE allele having a carboxyterminal deletion, and from Example 4, which plasmid contains a feedback-resistant cysE allele containing a variety of base substitutions.

The plasmids resulting from this cloning were designated pACYC184/cysE-Del in accordance with the extent of their deletion (cf. FIG. 9 for the plasmid map). Determination of the enzymic activity and the inhibitor constant, $K_i$, and also the cross-feeding test, were carried out in analogy with the description in Example 1. DNA sequence analysis was used to confirm that the deletions had been correctly introduced.

The results of these investigations are compiled in Tab. 6.

TABLE 5

Antisense oligonucleotides for preparing cysE alleles possessing carboxyterminal deletions

| SEQ ID. NO. | Mutation oligonucleotide | Nucleotide sequence | Position in FIG. 6 |
| --- | --- | --- | --- |
| 10 | cysE-Del270 | See FIG. 14 | 1006–1032 |
| 11 | cysE-Del268 | See FIG. 14 | 1000–1026 |
| 12 | cysE-Del263 | See FIG. 14 | 985–1011 |
| 13 | cysE-Del259 | See FIG. 14 | 973–999 |
| 14 | cysE-Del258 | See FIG. 14 | 970–996 |
| 15 | cysE-Del257 | See FIG. 14 | 966–993 |
| 16 | cysE-Del256 | See FIG. 14 | 964–990 |
| 17 | cysE-Del255 | See FIG. 14 | 961–987 |
| 18 | cysE-Del250 | See FIG. 14 | 946–972 |
| 19 | cysE-Del249 | See FIG. 14 | 943–969 |
| 20 | cysE-Del248 | See FIG. 14 | 940–966 |
| 21 | cysE-Del245 | See FIG. 14 | 931–957 |
| 22 | cysE-Del239 | See FIG. 14 | 913–939 |
| 23 | cysE-Del227 | See FIG. 14 | 877–903 |

The moiety written in bold corresponds to the respective bases in the sequence in FIG. 6; the NsiI site is underlined.

TABLE 6

Feedback-resistant cysE alleles produced by carboxyterminal deletions

| cysE mutant | Number of deleted amino acids | Terminal amino acids | $K_i$ ($\mu$M) |
| --- | --- | --- | --- |
| cysE-Del259 | 14 | His259 | 7.5 |
| cysE-Del258 | 15 | Gln258 | 5 |
| cysE-Del257 | 16 | Asp257 | 7.5 |
| cysE-Del256 | 17 | Met256 | 12.5 |
| cysE-Del255 | 18 | Asp255 | 30 |
| cysE-Del250 | 23 | Asp250 | 20 |
| cysE-Del249 | 24 | Ser249 | 15 |
| cysE-Del248 | 25 | Asp248 | 12.5 |

EXAMPLE 4

Transformation of an *E. coli* host strain with altered serine acetyltransferases for the purpose of over-producing L-cysteine or L-cysteine-related products in shaking flasks The vector pACYC184-LH, which is characterized by a low copy number, was used for the production. For this purpose, the cysE genes on the plasmids from Examples 1 and 2 were amplified by PCR.

The PCR experiments were carried out in 30 cycles in a thermocycler (Gene ATAQ Controller, from Pharmacia) in the presence of 200 $\mu$M deoxynucleotide triphosphates (dATP, dCTP, dGTP and dTTP), in each case 1 $\mu$M of the oligonucleotides of the sense primer cysE-LHfwl (SEQ ID NO: 9) and the corresponding antisense primer cysE-LHrevl (SEQ ID NO: 24), 10 ng of the respective plasmid DNA, reaction buffer (10 mM Tris-HCl pH 8.3, 50 mM KCl, 1.5 mM MgCl$_2$, 0.01% gelatin) and 5 units of a heat-stable Vent DNA polymerase (from Biolabs) and under the following conditions: 96° C., 1.5 min; 62° C., 1 min; 72° C., 3 min. cysE-LHfwl (SEQ ID NO: 9)

This nucleotide sequence is shown in FIG. 13.

The underlined bases correspond to the incorporated BstXI and SacI restriction cleavage sites; the remaining bases, printed in bold, correspond to positions 9–30 of the cysE sequence in FIG. 6.

cysE-LHrevl (SEQ ID NO: 24),

This nucleotide sequence is shown in FIG. 15.

The underlined bases correspond to the incorporated NsiI restriction cleavage sites; the remaining bases, which are printed in bold, correspond to positions 1106–1127 of the cysE sequence in FIG. 6.

The product which was obtained after the amplification was restricted with the enzymes SacI and NsiI and then purified through an agarose gel; the cysE DNA fragment which was isolated in each case was then ligated into vector pACYC184-LH (DSM 10172) which had been linearized with SacI and NsiI.

Each ligase mixture was transformed into the cysteine-auxotrophic cysE strain JM15 (CGSC#5042) and selection was carried out on cysteine-free, tetracycline-containing (20 mg/L) minimal medium. The series of feedback-resistant cysE plasmids which were obtained from this cloning were designated pACYC184/cysE (cf. FIG. 9), with each clone being provided with the corresponding cysE allele number.

Determination of the enzymic activity and of the inhibitor constant $K_i$, and also the cross-feeding test, were carried out in analogy with the description in Example 1.

In order to determine the production capacity in liquid medium, 20 ml of the standard production medium were inoculated with a single colony and incubated at 30° C. and 170 rpm for 48 hours. The production medium consisted of 15 g/L glucose, 0.08 g/L bactotryptone, 0.04 g/L yeast extract, 5 mg/L vitamin B1, 3 g/L KH$_2$PO$_4$, 12 g/L K$_2$HPO$_4$, 0.3 g/L MgSO$_4$×7 H$_2$O, 0.1 g/L NaCl, 5 g/L (NH$_4$)$_2$SO$_4$, 14.7 mg/L CaCl$_2$×2 H$_2$O, 2 mg/L FeSO$_4$×2 H$_2$O, 1 g/L Na$_3$ citrate×2 H$_2$O, 5 g/L Na$_2$S$_2$O$_3$×5 H$_2$O, 1 ml/L trace element solution and 0.025 mg/L tetracycline. The trace element solution was composed of 0.15 g/L Na$_2$MoO$_4$×2 H$_2$O, 2.5 g/L H$_3$BO$_3$, 0.7 g/L CoCl$_2$×6 H$_2$O, 0.25 g/L CuSO$_4$×5 H$_2$O, 1.6 g/L MnCl$_2$×4 H$_2$O and 0.3 g/L ZnSO$_4$×7 H$_2$O. A sample (10 $\mu$l) was in each case removed after 24 and 48 hours and diluted appropriately; the cysteine concentration in the cell-free supernatant was then determined calorimetrically using the method of Gaitonde, M. K. (1967), Biochem. J. 104, 627–633. In this context, concentration of between 50 and 300 mg of cysteine/L were measured for the production strain JM15 when transformed with different cysE mutants.

EXAMPLE 5

Construction of chromosomally encoded, feedback-resistant cysE alleles using a recombinant λ prophage, and production of L-cysteine or products derived from L-cysteine in a 1 L fermenter For the purpose of being integrated into the chromosomal attachment site (attλ), the cysE alleles cysEIV, cysEX and cysEXI were cloned into the plasmid pRS551 (Simons et al., 1987, Gene 53: 85–96). For this, each cysE allele was amplified by PCR from the corresponding cysE plasmid. The oligonucleotides which were used, i.e. cysE-fwl and cysE-revl, are described in Example 1. The amplification was carried out as described in Example 3. The resulting fragments were cleaved with EcoRI/BamHI, purified through an agarose gel and ligated into vector pRS551 which had been cleaved with EcoRI and BamHI. This afforded the vector pRS551-based recombinant plasmids pRScysEIV, X and XI.

A heterogeneous lambda lysate, which contained recombinant cysE allele-carrying λRS45 derivatives in addition to λRS45 phages, was produced in vivo by homologous recombination by means of preparing a plate lysate on a pRScysE-carrying recA+strain (e.g. YMC9, ATCC 3397) using the λRS45 phage (Simons et al., 1987, Gene 53: 85–96).

The cysE strain JM15, which was infected with the heterogeneous lambda lysate and subsequently plated on kanamycin-containing (25 mg/L) LB plates, was used for selecting for the recombinant RS45 derivatives. The lysogenic, kanamycin-resistant clones which were obtained were then tested for their ability to grow on minimal medium plates without cysteine. A clone which was in each case cysteine-prototrophic was selected and used for preparing a homogeneous cysE λ lysate (by means of UV induction, Simons et al., 1987, Gene 53: 85–96).

The JM15 stain was infected with these homogeneous cysE λ lysates which were obtained in each case. The resulting JM15attλ::cysE strains were cultured as described in Example 6. Instead of tetracycline, the respective media in each case contained 25 mg of kanamycin per L as the selection agent.

The yields of cysteine were: in the case of cysEIV, 0.5, in the case of cysEX, 1.8, and in the case of cysEXI, 2.1 g/L (cf. Tab. 7).

EXAMPLE 6

Influence of different, plasmid-encoded cysE alleles on the production of L-cysteine or products derived from L-cysteine in a 1 L fermenter using the host strain JM15 20 mL of LB medium (1% tryptone, 0.5% yeast extract, 0.5% NaCl) contained in a 100 mL Erlenmeyer flask were inoculated with a single colony of the production strain JM15 (CGSC#5042) which had been transformed with the respective cysE plasmid.

After having been incubated for 7 hours in a bacterial shaker (30° C., 150 rpm), the respective preliminary cultures were transferred to 100 mL of SM1 medium. The SM1 medium contained 5 g/L glucose, 5 mg/L vitamin B1, 3 g/l $KH_2PO_4$, 12 g/L $K_2HPO_4$, 0.3 g/L $MgSO_4 \times 7\ H_2O$, 0.1 g/L NaCl, 5 g/L $(NH4)_2SO_4$, 14.7 mg/L $CaCl_2 \times 2\ H_2O$, 2 mg/L $FeSO_4 \times 2\ H_2O$, 1 g/L $Na_3$ citrate$\times 2\ H_2O$, 1 ml/L trace element solution and 25 mg/L tetracycline. The trace element solution was composed of 0.15 g/L $Na_2MoO_4 \times 2\ H_2O$, 2.5 g/L $H_3BO_3$, 0.7 g/L $CoCl_2 \times 6\ H_2O$, 0.25 g/L $CuSO_4 \times 5\ H_2O$, 1.6 g/L $MnCl_2 \times 4\ H_2O$ and 0.3 g/L $ZnSO_4 \times 7\ H_2O$. The cultures were shaken in 1 L Erlenmeyer flasks at 30° C. and at 150 rpm for 17 h. After this incubation, the $OD_{600}$ was between 4 and 5. The subsequent fermentation was carried out in Braun-Melsungen BIOSTAT M research fermenters. A culturing vessel having a total volume of 2 L was used.

The fermentation medium contained 15 g/L glucose, 5 g/L NaCl, 0.3 g/L $MgSO_4 \times 7\ H_2O$, 15 mg/L $CaCl_2 \times 2\ H_2O$, 75 mg/L $FeSO_4 \times 7\ H_2O$, 1 g/L $Na_3$ citrate$\times 2\ H_2O$, 1.5 g/L $KH_2PO_4$, 1 mL of trace element solution (see above), 5 mg/L vitamin B1, 2.5 g/L yeast extract (Difco), 2.5 g/L tryptone (Difco) and 25 mg/L tetracycline.

The glucose concentration in the fermenter was initially adjusted to a value of 15 g/L by pumping in a 700 g/L (w/v) (sterilized) glucose solution, and the pH was adjusted to 7.0 by pumping in a 25% $NH_4OH$ solution. After an $OD_{600}$ of 10 had been reached, 300 mg per hour were supplied from a sterile 100 g/L (w/v) stock solution of thiosulfate. 100 mL of preliminary culture were pumped into the fermenter vessel for the inoculation. The starting volume was approximately 1 L. The cultures were initially stirred at 400 rpm and aerated with 1.5 vvm of compressed air which had been sterilized by passing through a sterile filter. The fermentation was carried out at a temperature of 30° C.

The pH was maintained at a value of 7.0 by means of automatic correction with 25% $NH_4OH$. The oxygen saturation in the fermentation broth had at no time during the fermentation to fall below 20%; the stirring speed was used to ensure this. The glucose content of the nutrient solution, the optical density and the cysteine content were determined at two- to three-hourly intervals. The glucose content was determined enzymically using a glucose analyzer from YSI. The concentration of the glucose was adjusted to between 10 and 20 g/L by means of continuously feeding in this compound.

The content of cysteine in the medium was determined calorimetrically from the cell-free super-natant of the sample using the method of Gaitonde, M. K. (1967), Biochem. J. 104, 627–633.

The fermentation was terminated after 44–50 h. The quantities of cysteine, in g/L, which were produced after 48 h are summarized in Table 7.

TABLE 7

Cysteine yield of the production strain JM15, which is transformed with different cysE alleles (1L fermenter)

| cysE allele | Cysteine yield [g/L] [48 h] |
| --- | --- |
| pACYC184/cysEIV | 1.6 |
| pACYC184/cysEV | 1.3 |
| pACYC184/cysEVI | 1.4 |
| pACYC184/cysEX | 3.4 |
| pACYC184/cysEXI | 3.4 |
| pACYC184/cysEXII | 1.2 |
| pACYC184/cysEXIV | 2.3 |
| pACYC184/cysEXV | 3.0 |
| pACYC184/cysEXVI | 2.2 |
| pACYC184/cysEXXIII | 2.7 |
| pACYC184/cysEDe1255 | 3.9 |

EXAMPLE 7

Production of L-cysteine or products derived from L-cysteine using corynebacteria The feedback-resistant cysE alleles, cysEIV, cysEX, cysEXI and cysEXIV (cf. Tab. 2 in Example 1), were cleaved out of their corresponding plasmids using the restriction enzymes BamHI and EcoRI (from Boehringer Mannheim) and each respective 1.15 kb-sized DNA fragment was purified through an agarose gel and isolated. The respective DNA fragment was rendered blunt-ended using the Klenow fragment of E. coli DNA polymerase I (from Boehringer Mannheim). The vector pWST1 was hydrolyzed with the restriction enzyme SmaI (from Boehringer Mannheim) and ligated to the blunt-ended DNA fragment using T4 DNA ligase. The vector pWST1 is an E. coli/Corynebacterium shuttle vector and can replicate both in E. coli and in corynebacteria. The corynebacterial replicon of this vector originates from the Corynebacterium glutamicum strain ATCC 19223. The preparation of vector pWST1 is described in U.S. Pat. No. 4,965,197. The ligation mixture was used to transform the mutant JM15, which is auxotrophic for cysteine. The complementing plasmids were designated pWST1-cysEIV, pWST1-cysEX, pWST1-cysEXI and pWST1-cysEXIV in accordance with their inserted cysE alleles.

The pWST1-cysE plasmids were used to transform the Corynebacterium glutamicum ATCC21851. The transformation was carried out by electroporation using the technique described in detail in Liebl, W. et al., 1989, FEMS Microbiol. Letters, 65, 299–304. The recombinant clones were selected on the basis of their plasmid-encoded resistance to kanamycin on agar plates containing 25 mg/L kanamycin.

The fermentation was carried out in analogy with the conditions described in Example 6 except that kanamycin, at a concentration of 50 mg/L, was used as the selection antibiotic instead of tetracycline.

It was found in the fermentation that the strain carrying the cysEXI allele on a plasmid achieves the highest cysteine yields.

What is claimed is:

1. A recombinant serine acetyltransferase which exhibits a sensitivity to the inhibitor L-cysteine which is reduced in comparison to the wild-type enzyme and whose protein sequence exhibits at least one mutation or deletion when compared with the wild-type sequence, wherein the mutation is in the sequence region of amino acids 97–100, 164–169, 237, 239–240, 245–259 and 267–269 or the deletion is in the carboxyterminal sequence region of amino acids 237–240, 245–259 and 267–269, with position 1 being the start methionine in SEQ ID NO: 1 and with the mutation of Met to Ile in position 256 being excluded, and wherein the serine acetyltransferase has an inhibitor constant, $K_i$, of from 0.02 to 2.3 mM in the presence of 1 mM L-serine and 0.1 mM acetyl-CoA.

2. A recombinant serine acetyltransferase which exhibits a sensitivity to the inhibitor L-cysteine which is reduced in comparison to the wild-type enzyme and whose protein sequence exhibits at least one mutation or deletion when compared with the wild-type sequence, wherein the mutation is in the sequence region of amino acids 97–100, 164–169, 237, 239–240, 245–255, 257–259 and 267–269 or the deletion is in the carboxyterminal sequence region of amino acids 237–240, 245–255, 257–259 and 267–269, with position 1 being the start methionine of SEQ ID NO: 1.

3. A recombinant DNA sequence which encodes a serine acetyltransferase as claimed in claim 1.

4. An recombinant DNA sequence which encodes a serine acetyltransferase as claimed in claim 2.

5. A transformed microorganism which possesses a cysteine metabolism and which is regulated by at least one DNA sequence as claimed in claim 3.

6. A transformed microorganism which possesses a cysteine metabolism and which is regulated by at least one DNA sequence as claimed in claim 4.

* * * * *